United States Patent
Majid et al.

(10) Patent No.: US 7,132,428 B2
(45) Date of Patent: Nov. 7, 2006

(54) PYRAZOLOISOQUINOLINE DERIVATIVE AS KINASE INHIBITORS FOR THE TREATMENT OF VARIOUS DISORDERS

(75) Inventors: Tahir Nadeem Majid, Hoboken, NJ (US); Corey Hopkins, Hillsborough, NJ (US); Brian Leslie Pedgrift, Flemington, NJ (US); Nicola Collar, Jersey City, NJ (US); Friederike Wirtz-Brugger, Branchburg, NJ (US); Jean Merrill, Whippany, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 163 days.

(21) Appl. No.: 10/613,588

(22) Filed: Jul. 3, 2003

(65) Prior Publication Data
US 2005/0009859 A1    Jan. 13, 2005

(51) Int. Cl.
*A61K 31/437* (2006.01)
*C07D 471/04* (2006.01)
*C07D 471/12* (2006.01)

(52) U.S. Cl. ............ 514/293; 514/292; 514/269; 546/82

(58) Field of Classification Search ............ 546/82; 544/353; 514/293, 292, 249
See application file for complete search history.

(56) References Cited

U.S. PATENT DOCUMENTS

| 4,748,246 A | 5/1988 | Skotnicki et al. |
| 6,841,556 B1 * | 1/2005 | Flohr et al. ........... 514/293 |

FOREIGN PATENT DOCUMENTS

| EP | 1134221 | 9/2001 |
| GB | 2185255 | 7/1987 |
| WO | WO 02/44153 | 6/2002 |
| WO | WO 03/024936 | 3/2003 |

OTHER PUBLICATIONS

Yumi Yamamoto et al., Role of the NF-kB Pathway in the Pathogenesis of Human Disease States, Current Molecullar Medicine (2001, pp. 287-296, vol. 1).

Lucia Cecchi et al., Synthesis of 1,5-Diaryl-3-Methyl-1 H-pyrazolo(4,5-c) Isoquinolines And Studies of Binding to Specific Peripheral Benzodiazepine Binding Sites, Journal of Pharmaceutical Sciences (1989, pp. 437-442, vol. 78, No. 6).

* cited by examiner

*Primary Examiner*—Rita Desai
(74) *Attorney, Agent, or Firm*—Balaram Gupta

(57) ABSTRACT

Compounds of the formula I

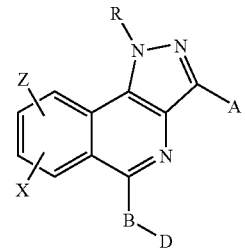

are suitable for producing pharmaceuticals for the prophylaxis and therapy of diseases whose course involves an increased activity of NIK.

5 Claims, No Drawings

PYRAZOLOISOQUINOLINE DERIVATIVE AS KINASE INHIBITORS FOR THE TREATMENT OF VARIOUS DISORDERS

The invention relates to novel pyrazoloisoquinoline derivatives, to processes for preparing them and to their use as pharmaceuticals, in particular their use for inhibiting kinases. More particularly, their use for inhibiting NFκB-inducing kinase (NIK). The pyrazoloisoquinoline derivatives can therefore be used for treating a variety of disease conditions that involve inflammatory component due to increase in NIK activity, particularly multiple sclerosis (MS).

NFκB is a heterodimeric transcription factor which is able to activate a large number of genes which encode, inter alia, proinflammatory cytokines such as IL-1, IL-2, TNFα or IL-6. NFκB is present in the cytosol of cells, where it is complexed with its naturally occurring inhibitor IκB. Stimulation of the cells, for example by cytokines, leads to the IκB being phosphorylated and subsequently broken down proteolytically. This proteolytic breakdown leads to the activation of NFκB, which then migrates into the nucleus of the cell, where it activates a large number of proinflammatory genes.

In diseases such as rheumatoid arthritis (in connection with inflammation), osteoarthritis or asthma, NFκB is activated beyond the normal extent. It has been demonstrated that pharmaceuticals such as glucocorticoids, salicylates or gold salts, which are used in the therapy of rheumatism, inhibit the NFκB-activating signal chain at various points or interfere directly with the transcription of the genes.

IkB kinase (IKK) has a central function in the NFκB signal transduction pathway since it mediates the phosphorylation of IkB. IKK is likewise activated by phosphorylation. The NFκB-inducing kinase (NIK) is a Ser/Thr kinase and participates in the activation of IKK. By means of overexpressing NIK in cell culture, it was possible to augment, in a stimulus-independent manner, the expression of NFκB-activated reporter genes or the expression of the NFκB-induced adhesion molecule ICAM1. NIK mediates this effect by interacting with, and phosphorylating, the IKKα sub-unit of IKK. By contrast, it was possible to inhibit the expression of an NFκB-activated reporter gene, and the IL1-induced expression of the adhesion molecule ICAM1, by overexpressing a dominant negative NIK mutant in cell culture. It was possible, by overexpressing the NIK C-terminal domain, which is responsible for interacting with IKK, to inhibit the TNFα-induced expression of an NFκB-activated reporter gene in cell culture. Pyrazoloisoquinoline derivatives which possess inhibitory activity directed against NIK are likewise able to inhibit the release of TNFα in LPS-stimulated and IL1β-stimulated human peripheral blood lymphocytes as well as the release of IL1β, TNFα and IL6 in LPS-stimulated whole human blood. Pyrazoloisoquinoline compounds possessing anti-inflammatory activity have already been described in the published document GB 2 185 255 A.

In the endeavor to obtain effective compounds for treating diseases whose course involves an increased activity of NFκB-inducing kinase, it has now been found that the pyrazoloisoquinoline derivatives according to the invention are strong and very specific inhibitors of NIK and exhibit good solubility in water.

The invention therefore relates to the compounds of the formula I

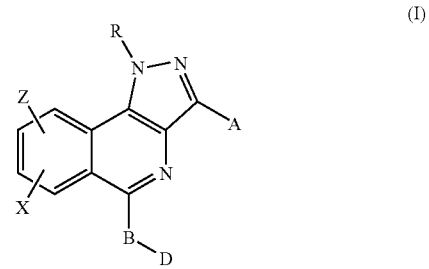

(I)

or a stereoisomeric form or a pharmaceutically acceptable salt of the compound of the formula I, wherein
A is —$(C_1-C_6)$-alkyl, in which alkyl is straight-chain or branched and is optionally substituted, once or more, independently of each other, by
—O—$R^1$ or
—C(O)—$OR^1$,
—C(O)—$NR^1R^1$,
—C(O)—$NR^1$—$SO_2R^1$,
—$NR^1R^1$,
—CN, in which $R^1$ is
hydrogen,
—$(C_1-C_6)$-alkyl,
—$(C_6-C_{14})$aryl or
fluoroalkyl of the formula —$C_nH_xF_y$ or fluoroalkoxy of the formula —$OC_nH_xF_y$, wherein n is an integer from 1 to 6, x is an integer from 0 to 12, y is an integer from 1 to 13 and sum of x and y is 2n+1,
—O—$R^1$,
—$SR^1$,
—S(O)—$R^1$,
—$S(O)_2$—$R^1$,
—C(O)—$OR^1$,
fluoroalkyl of the formula —$C_nH_xF_y$ or fluoroalkoxy of the formula —$OC_nH_xF_y$, wherein n is an integer from 1 to 6, x is an integer from 0 to 12, y is an integer from 1 to 13 and, sum of x and y is 2n+1,
—C(O)—$NR^1R^1$,
—C(O)—$NR^1$—$SO_2R^1$,
—$NR^1R^1$,
—CN,
heteroaryl having from 5 to 14 ring members, in which heteroaryl is unsubstituted or optionally substituted once or more, independently of each other, by $R^2$, in which $R^2$ is
—$(C_1-C_4)$-alkyl,
—OH,
—O—$(C_1-C_4)$-alkyl,
halogen,
—N($R^3$)—$R^4$ in which $R^3$ and $R^4$ are, independently of each other, hydrogen atom or —$(C_1-C_4)$-alkyl,
fluoroalkyl of the formula —$C_nH_xF_y$ or fluoroalkoxy of the formula —$OC_nH_xF_y$, wherein n is an integer from 1 to 4, x is an integer from 0 to 8, y is an integer from 1 to 9 and sum of x and y is 2n+1,
—CN,
—$SR^1$,
—S(O)—$R^1$,
—$S(O)_2$—$R^1$ or
—C(O)—$NR^1R^1$, —($C_3$–$C_6$)-cycloalkyl, in which cycloalkyl is unsubstituted or substituted, once or more, independently of each other, by $R^2$, and $R^2$ is defined as above, heterocycle having from 5 to 12 ring members, in which heterocycle is unsubstituted or substituted, once or more, independently of each other, by $R^2$ and $R^2$ is defined as above, B is a covalent bond,
—C═$CR^1$—,
—C≡C—,
—O($CH_2$)$_a$—, in which a is an integer from 1 to 4,
O, S, $NR^2$, —C(O)—, —$NR^2$—C(O)—, —C(O)—$NR^2$—, —$NR^2$—$SO_2$—, —$SO_2$—$NR^2$—, —$NR^2$—C(O)—$NR^2$—, and $R^2$ is defined as above, or
—($C_1$–$C_4$)-alkylene, in which alkylene is straight-chain or branched and is optionally substituted, once or more, independently of each other, by $R^1$, and $R^1$ is defined as above, D is —($C_1$–$C_6$)-alkyl, in which alkyl is straight-chain or branched and is optionally substituted, once or more, independently of each other, by $R^1$, and $R^1$ is defined as above, heteroaryl having from 5 to 14 ring members, in which heteroaryl is unsubstituted or is substituted once or more, independently of each other, by $R^2$ and $R^2$ is defined as above, heterocycle having from 5 to 12 ring members, in which heterocycle is unsubstituted or substituted, once or more, independently of each other, by $R^2$ and $R^2$ is defined as above, —($C_6$–$C_{14}$)-aryl, in which aryl is unsubstituted or substituted, once or more, independently of each other, by $R^2$ and $R^2$ is defined as above, or —($C_3$–$C_6$)-cycloalkyl, in which cycloalkyl is unsubstituted or substituted, once or more, independently of each other, by $R^2$ and $R^2$ is defined as above, or B-D is hydrogen,
halogen,
fluoroalkyl of the formula —$C_nH_xF_y$ or fluoroalkoxy of the formula —$OC_nH_xF_y$, wherein n is an integer from 1 to 4, x is an integer from 0 to 8, y is an integer from 1 to 9 and sum of x and y is 2n+1,
—($CH_2$)$_a$—Y—$R^3$, in which a is an integer from 1 to 4, Y is O, S, $NR^2$, and $R^3$ is
—($C_1$–$C_6$)-alkyl,
—($C_6$–$C_{14}$)-aryl,
—($C_3$–$C_6$)-cycloalkyl, and R is hydrogen,
—($C_1$–$C_6$)-alkyl, or
—($C_6$–$C_{14}$)-aryl-($C_1$–$C_6$)-alkyl, in which aryl is unsubstituted or substituted, once or more, independently of each other, by $R^2$ and $R^2$ is defined as above, and X and Z are identical or different and are, independently of each other selected from:
hydrogen atom,
—($C_1$–$C_4$)-alkyl,
—OH,
—O—($C_1$–$C_4$-alkyl),
halogen,
fluoroalkyl of the formula —$C_nH_xF_y$ or fluoroalkoxy of the formula —$OC_nH_xF_y$, wherein n is an integer from 1 to 6, x is an integer from 0 to 12, y is an integer from 1 to 13 and sum of x and y is 2n+1,
—C(O)—$OR^1$,
—C(O)—$NR^1R^1$,
—C(O)—$NR^1$—$SO_2R^1$,
—$NR^1R^1$,
—$NR^1$—C(O)—$NR^1R^1$,
—$NR^1$—C(O)—$R^1$,
—$NR^1$—C(O)—$OR^1$,
—O—C(O)—$NR^1R^1$,
—CN,
—$SR^1$,
—S(O)—$R^1$,
—S(O)$_2$—$R^1$,
—S(O)$_2$—$NR^1R^1$,
—$NR^1$—$SO_2$—$R^1$, in which $R^1$ is as defined above, heterocycle having from 5 to 12 ring members, in which heterocycle is unsubstituted or substituted, once or more, independently of each other, by $R^2$, and $R^2$ is defined as above, or —($C_3$–$C_6$)-cycloalkyl, in which cycloalkyl is unsubstituted or substituted, once or more, independently of each other, by $R^2$, and $R^2$ is defined as above, with the proviso that when A is —($C_1$–$C_6$)-alkyl, —O—$R^1$, —C(O)—$OR^1$, or heteroaryl, at least one of the following applies:

B is not a covalent bond or —($C_1$–$C_4$)-alkylene,
D is not heteroaryl, heterocycle, —($C_6$–$C_{14}$)-aryl, —($C_3$–$C_6$)-cycloalkyl, or
X and Z are not —($C_1$–$C_4$)-alkyl, —OH, —O—($C_1$–$C_4$)-alkyl, or halogen.

The invention further more relates to compound of the formula (I), wherein

A is —($C_1$–$C_3$)-alkyl, in which alkyl is straight-chain or branched and is optionally substituted, once or more, independently of each other, by
—O—$R^1$, or
—C(O)—$OR^1$, in which $R^1$ is
hydrogen,
—($C_1$–$C_3$)-alkyl, or
—$CF_3$
fluoroalkyl of the formula —$C_nH_xF_y$ or fluoroalkoxy of the formula —$OC_nH_xF_y$, wherein n is an integer from 1 to 3, x is an integer from 0 to 6, y is an integer from 1 to 7 and sum of x and y is 2n+1, B is a covalent bond or O,
D is phenyl or naphthyl, in which phenyl or naphthyl is unsubstituted or substituted, once or more, independently of each other, by $R^2$, in which $R^2$ is
fluorine, chlorine or bromine,
—OH,
—$CF_3$,
—$SR^1$, in which $R^1$ is defined as above,
—($C_1$–$C_4$)-alkyl
—O—($C_1$–$C_2$)-alkyl or
—N($R^3$)—$R^4$ in which $R^3$ and $R^4$ are, independently of each other, hydrogen atom or —($C_1$–$C_3$)-alkyl, heteroaryl selected from the group consisting of pyridyl, furanyl, pyrrolyl, isoxazolyl, benzofuranyl, benzothiophenyl, quinolinyl, isoquinolinyl, quinoxalinyl and thiophenyl, in which heteroaryl is unsubstituted or substituted, once or more, independently of each other, by $R^2$, in which $R^2$ is defined as above, or —($C_4$–$C_6$)-cycloalkyl, in which cycloalkyl is unsubstituted or substituted, once or more, independently of each other, by $R^2$, and $R^2$ is defined as above, and R is hydrogen,
—($C_1$–$C_3$)-alkyl, or
-phenyl-($C_1$–$C_3$)-alkyl, and X and Z are identical or different and are, independently of each other, hydrogen —C(O)—O($C_1$–$C_3$)alkyl, —$OCH_3$, —N($CH_3$)$_2$ or halogen.

The invention furthermore relates to compounds of the formula I which are selected from the following group:
5-pyridin-2-yl-3-trifluoromethyl-1H-pyrazolo[4,3-c]isoquinoline,
3-methyl-5-(2-trifluoromethyl-phenyl)-1H-pyrazolo[4,3-c]isoquinoline,
3-methyl-5-(3-trifluoromethyl-phenyl)-1H-pyrazolo[4,3-c]isoquinoline,
3-methyl-5-(4-trifluoromethyl-phenyl)-1H-pyrazolo[4,3-c]isoquinoline,
1,3-dimethyl-5-(3-trifluoromethylphenyl)-1H-pyrazolo[4,3-c]-isoquinoline,
5-phenyl-3-trifluoromethyl-1H-pyrazolo[4,3-c]isoquinoline,
1,3-dimethyl-5-(3-trifluoromethylphenyl)-1H-pyrazolo[4,3-c]-isoquinoline,
1,3-dimethyl-5-(2,6-difluorophenyl)-1H-pyrazolo[4,3-c]-isoquinoline,
1-benzyl-5-cyclohexyl-3-methyl-1H-pyrazolo[4,3-c]-isoquinoline,
1-benzyl-5-naphthyl-3-methyl-1H-pyrazolo[4,3-c]-isoquinoline,
5-methoxymethyl-3-methyl-1H-pyrazolo[4,3-c]-isoquinoline,
7-methoxycarbonyl-3-methyl-5-phenyl-1H-pyrazolo[4,3-c]-isoquinoline,
7-methoxycarbonyl-3-methyl-5-pyridin-2-yl-1H-pyrazolo[4,3-c]-isoquinoline,
7-dimethylamino-3-methyl-5-phenyl-1H-pyrazolo[4,3-c]isoquinoline,
7-dimethylamino-3-methyl-5-pyridin-2-yl-1H-pyrazolo[4,3-c]-isoquinoline,
6-dimethylamino-3-methyl-5-phenyl-1H-pyrazolo[4,3-c]isoquinoline,
6-dimethylamino-3-methyl-5-pyridin-2-yl-1H-pyrazolo[4,3-c]-isoquinoline,
8-dimethylamino-3-methyl-5-phenyl-1H-pyrazolo[4,3-c]isoquinoline,
8-dimethylamino-3-methyl-5-pyridin-2-yl-1H-pyrazolo[4,3-c]-isoquinoline,
1,3-dimethyl-5-(3-methyl-thiophen-2-yl)-1H-pyrazolo[4,3-c]-isoquinoline,
3-methyl-5-phenyl-9-trifluoromethyl-1H-pyrazolo[4,3-c]isoquinoline,
3-methyl-5-pyridin-2-yl-9-trifluoromethyl-1H-pyrazolo[4,3-c]-isoquinoline, and
3-methyl-5-(2,3,4,5,6-pentafluoro-phenyl)-1H-pyrazolo[4,3-c]isoquinoline.

In another aspect of the invention the invention also relates to further compounds within the scope of formula (I) which are selected from the following group:
5-benzo[b]thiophene-2yl-3-methyl-1H-pyrazolo[4,3-c]isoquinoline,
7-bromo-3-methyl-5-phenyl-1H-pyrazolo[4,3-c]isoquinoline,
7-bromo-3-methyl-5-pyridin-2-yl-1H-pyrazolo[4,3-c]isoquinoline,
5-(3-chloro-benzo[b]thiophen-2-yl)-3-methyl-1H-pyrazolo[4,3-c]-isoquinoline,
5-(2-chloro-pyridin-3-yl)-3-methyl-1H-pyrazolo[4,3-c]isoquinoline,
5-(6-chloro-pyridin-3-yl)-3-methyl-1H-pyrazolo[4,3-c]isoquinoline,
3-ethyl-5-phenyl-1H-pyrazolo[4,3-c]isoquinoline,
3-ethyl-5-pyridin-2-yl-1H-pyrazolo[4,3-c]isoquinoline,
3-ethyl-5-pyridin-3-yl-1H-pyrazolo[4,3-c]isoquinoline,
5-furan-2-yl-3-methyl-1H-pyrazolo[4,3-c]isoquinoline,
7-methoxy-3-methyl-5-pyridin-2-yl-1H-pyrazolo[4,3-c]isoquinoline,
3-methyl-5-(3-methyl-benzofuran-2-yl)-1H-pyrazolo[4,3-c]-isoquinoline,
3-methyl-5-phenyl-1H-pyrazolo[4,3-c]isoquinoline,
6-chloro-3-methyl-5-phenyl-1H-pyrazolo[4,3-c]isoquinoline,
6-fluoro-3-methyl-5-phenyl-1H-pyrazolo[4,3-c]isoquinoline,
8-chloro-3-methyl-5-phenyl-1H-pyrazolo[4,3-c]isoquinoline,
8-fluoro-3-methyl-5-phenyl-1H-pyrazolo[4,3-c]isoquinoline,
9-chloro-3-methyl-5-phenyl-1H-pyrazolo[4,3-c]isoquinoline,
9-fluoro-3-methyl-5-phenyl-1H-pyrazolo[4,3-c]isoquinoline,
3,9-dimethyl-5-phenyl-1H-pyrazolo[4,3-c]isoquinoline,
3-methyl-5-(2-methyl-phenyl)-1H-pyrazolo[4,3-c]isoquinoline,
3-methyl-5-(3-methyl-phenyl)-1H-pyrazolo[4,3-c]isoquinoline,
3-methyl-5-(4-methyl-phenyl)-1H-pyrazolo[4,3-c]isoquinoline,
3-methyl-5-(2-bromo-phenyl)-1H-pyrazolo[4,3-c]isoquinoline,
3-methyl-5-(3-bromo-phenyl)-1H-pyrazolo[4,3-c]isoquinoline,
3-methyl-5-(2-chloro-phenyl)-1H-pyrazolo[4,3-c]isoquinoline,
3-methyl-5-(4-chloro-phenyl)-1H-pyrazolo[4,3-c]isoquinoline,
3-methyl-5-(2,4-dichloro-phenyl)-1H-pyrazolo[4,3-c]isoquinoline,
3-methyl-5-(3,4-dichloro-phenyl)-1H-pyrazolo[4,3-c]isoquinoline,
3-methyl-5-(2,6-dichloro-phenyl)-1H-pyrazolo[4,3-c]isoquinoline,
3-methyl-5-(2-fluoro-phenyl)-1H-pyrazolo[4,3-c]isoquinoline,
3-methyl-5-(4-fluoro-phenyl)-1H-pyrazolo[4,3-c]isoquinoline,
3-methyl-5-(2,4-difluoro-phenyl)-1H-pyrazolo[4,3-c]isoquinoline,
3-methyl-5-(2,6-difluoro-phenyl)-1H-pyrazolo[4,3-c]isoquinoline,
6-chloro-3-methyl-5-pyridin-2-yl-1H-pyrazolo[4,3-c]isoquinoline,
6-fluoro-3-methyl-5-pyridin-2-yl-1H-pyrazolo[4,3-c]isoquinoline,
8-chloro-3-methyl-5-pyridin-2-yl-1H-pyrazolo[4,3-c]isoquinoline,
8-fluoro-3-methyl-5-pyridin-2-yl-1H-pyrazolo[4,3-c]isoquinoline,
9-chloro-3-methyl-5-pyridin-2-yl-1H-pyrazolo[4,3-c]isoquinoline,
9-fluoro-3-methyl-5-pyridin-2-yl-1H-pyrazolo[4,3-c]isoquinoline,
3,9-dimethyl-5-pyridin-2-yl-1H-pyrazolo[4,3-c]isoquinoline,
3-methyl-5-(1-methyl-1H-pyrrol-2-yl)-1H-pyrazolo[4,3-c]isoquinoline,
3-methyl-5-quinolin-2-yl-1H-pyrazolo[4,3-c]isoquinoline,
3-methyl-5-quinolin-3-yl-1H-pyrazolo[4,3-c]isoquinoline,
3-methyl-5-quinoxalin-2-yl-1H-pyrazolo[4,3-c]isoquinoline, 3-methyl-5-thiophen-2-yl-1H-pyrazolo[4,3-c]isoquinoline, and 3-methyl-5-(3-methyl-thiophen-2-yl)-1H-pyrazolo[4,3-c]isoquinoline.

The term "$(C_1–C_6)$-alkyl" is understood as meaning hydrocarbon radicals whose carbon chain is straight-chain or branched and contains from 1 to 6 carbon atoms, for example methyl, ethyl, propyl, isopropyl, butyl, isobutyl, tertiary-butyl, pentyl, isopentyl, neopentyl, hexyl, 2,3-dimethylbutane or neohexyl. Examples of $(C_3–C_6)$-cycloalkyl radicals are compounds which are derived from 3- to 6-membered monocycles such as cyclopropyl, cyclobutyl, cyclopentyl and cyclohexyl. The term "halogen" is understood as meaning fluorine, chlorine, bromine or iodine.

The term "aryl" is understood as meaning aromatic hydrocarbon radicals having from 6 to 14 carbon atoms in the ring. Examples of $(C_6–C_{14})$-aryl radicals are phenyl, naphthyl, for example 1-naphthyl and 2-naphthyl, biphenyl, for example 2-biphenyl, 3-biphenyl and 4-biphenyl, anthryl and fluorenyl. Biphenyl radicals, naphthyl radicals and, in particular, phenyl radicals are preferred aryl radicals. Aryl radicals, in particular phenyl radicals, can be substituted once or more than once, preferably once, twice or three times, by identical or different radicals, preferably by radicals from the series $(C_1–C_8)$-alkyl, in particular $(C_1–C_4)$-alkyl, $(C_1–C_8)$-alkoxy, in particular $(C_1–C_4)$-alkoxy, halogen, nitro, amino, trifluoromethyl, hydroxyl, hydroxy-$(C_1–C_4)$-alkyl, such as hydroxymethyl or 1-hydroxyethyl or 2-hydroxyethyl, methylenedioxy, ethylenedioxy, formyl, acetyl, cyano, hydroxycarbonyl, aminocarbonyl, $(C_1–C_4)$-alkoxycarbonyl, phenyl, phenoxy, benzyl, benzyloxy and tetrazolyl. The same applies, in a corresponding manner, for example, for radicals such as arylalkyl or arylcarbonyl. Arylalkyl radicals are, in particular, benzyl and also 1- and 2-naphthylmethyl, 2-, 3- and 4-biphenylmethyl and 9-fluorenylmethyl. Substituted arylalkyl radicals are, for example, benzyl radicals and naphthylmethyl radicals which are substituted, in the aryl moiety, by one or more $(C_1–C_8)$-alkyl radicals, in particular $(C_1–C_4)$-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, and 1-, 3-, 4-, 5-, 6-, 7- and 8-methyl-2-naphthylmethyl, benzyl radicals and naphthylmethyl radicals which are substituted, in the aryl moiety, by one or more $(C_1–C_8)$-alkoxy radicals, in particular $(C_1–C_4)$-alkoxy radicals, for example 4-methoxybenzyl, 4-neopentyloxybenzyl, 3,5-dimethoxybenzyl, 3,4-methylenedioxybenzyl, 2,3,4-trimethoxybenzyl, nitrobenzyl radicals, for example 2-, 3- and 4-nitrobenzyl, halobenzyl radicals, for example 2-, 3- and 4-chlorobenzyl, 2-, 3- and 4-fluorobenzyl, 3,4-dichlorobenzyl, pentafluorobenzyl and trifluoromethylbenzyl radicals, for example 3- and 4-trifluoromethylbenzyl and 3,5-bis(trifluoromethyl)benzyl.

In monosubstituted phenyl radicals, the substituent can be located in the 2 position, the 3 position or the 4 position. Doubly substituted phenyl can be substituted in the 2,3 position, the 2,4 position, the 2,5 position, the 2,6 position, the 3,4 position or the 3,5 position. In triply substituted phenyl radicals, the substituents can be located in the 2,3,4 position, the 2,3,5 position, the 2,4,5 position, the 2,4,6 position, the 2,3,6 position or the 3,4,5 position.

The comments made with regard to the aryl radicals apply, in a corresponding manner, to divalent arylene radicals, for example to phenylene radicals, which can be present, for example, as 1,4-phenylene or as 1,3-phenylene. Phenylene-$(C_1–C_6)$-alkyl is, in particular, phenylene-methyl ($—C_6H_4—CH_2—$) and phenyleneethyl, $(C_1–C_6)$-alkylenephenyl, in particular methylenephenyl ($—CH_2—C_6H_4—$). Phenylene-$(C_2–C_6)$-alkenyl is, in particular, phenyleneethenyl and phenylenepropenyl.

The phrase "heteroaryl having from 5 to 14 ring members" means a radical of a monocyclic or polycyclic aromatic system having from 5 to 14 ring members which contains 1, 2, 3, 4 or 5 heteroatoms as ring members. Examples of heteroatoms are N, O and S. If several heteroatoms are present, they may be identical or different. Heteroaryl radicals can also be substituted, once or several times, preferably once, twice or three times, by identical or different radicals from the series $—(C_1–C_8)$-alkyl, in particular $—(C_1–C_4)$-alkyl, $—(C_1–C_8)$-alkoxy, in particular $—(C_1–C_4)$-alkoxy, halogen, nitro, $—N(R^{10})_2$, trifluoromethyl, hydroxyl, hydroxy-$(C_1–C_4)$-alkyl, such as hydroxymethyl or 1-hydroxyethyl or 2-hydroxyethyl, methylenedioxy, formyl, acetyl, cyano, hydroxycarbonyl, aminocarbonyl, $—(C_1–C_4)$-alkoxycarbonyl, phenyl, phenoxy, benzyl, benzyloxy and tetrazolyl. Heteroaryl having from 5 to 14 ring members is preferably a monocyclic or bicyclic aromatic radical which contains 1, 2, 3 or 4, in particular 1, 2 or 3, identical or different heteroatoms from the series N, O and S, and which can be substituted by 1, 2, 3 or 4, in particular 1 to 3, identical or different substituents from the series $—(C_1–C_6)$-alkyl, $—(C_1–C_6)$-alkoxy, fluorine, chlorine, nitro, $—N(R^{10})_2$, trifluoromethyl, hydroxyl, hydroxy-$(C_1–C_4)$-alkyl, $—(C_1–C_4)$-alkoxycarbonyl, phenyl, phenoxy, benzyloxy and benzyl. Particularly preferably, heteroaryl is a monocyclic or bicyclic aromatic radical having from 5 to 10 ring members, in particular a 5-membered to 6-membered monocyclic aromatic radical which contains 1, 2 or 3, in particular 1 or 2, identical or different heteroatoms from the series N, O and S and which can be substituted by 1 or 2 identical or different substituents from the series $—(C_1–C_4)$-alkyl, halogen, hydroxyl, $—N(R^{10})_2$, $—(C_1–C_4)$-alkoxy, phenyl, phenoxy, benzyloxy and benzyl.

The term "heterocycle having from 5 to 12 ring members" means a monocyclic or bicyclic 5-membered to 12-membered heterocyclic ring which is partially saturated or completely saturated. Examples of heteroatoms are N, O and S. The heterocycle is unsubstituted or substituted by identical or different substituents at one or more carbon atoms or at one or more heteroatoms. These substituents have been defined above in connection with the heteroaryl radical.

Examples of the terms "heteroaryl having from 5 to 14 ring members" and "heterocycle having from 5 to 12 ring members" are radicals such as acridinyl, azaspirodecanyl, azepinyl, azetidinyl, aziridinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl, isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenyl, thiophenolyl, thiopyranyl, 1,2,3-triazinyl, 1,2,3-triazolyl, 1,2,3-triazolyl, 1,2,4-triazolyl, 1,2,5-triazolyl, 1,3,4-triazolyl and xanthenyl.

Preferred radicals are those derivable from benzodioxolane, benzofuran, benzothiazole, benzothiophene, benzoxazole, β-carboline, quinazoline, quinoline, quinoxaline, cinnoline, cyclohepta[b]-5-pyrrole, 4,5-dihydro-1,3-oxazole, dihydropyridine, 4,5-dihydro-1,3-thiazole, 1,3-dioxolane, furan, 3-hydroxypyrro-2,4-dione, imidazole, 2-imidazoline, imidazolidine, indazole, indole, indoline, isoquinoline, isoindole, isoindoline, isoxazolones, isothiazole, isoxazole, morpholine, oxadiazolidinedione, oxadiazolone, 1,2,3,5-oxathiadiazole 2-oxide, oxazole, 1,3-oxazolidine, 5-oxo-1,2,4-thiadiazole, perhydroazepine, perhydro-1,4-dioxane, phthalazine, piperazine, piperidine, pyrazine, pyrazole, pyridine, pyrimidine, pyrrole, pyrrolidine, pyrroline, tetrahydrofuran, 1,2,3,4-tetrahydroisoquinoline, tetrahydropyridine, 1,2,3,4-tetrahydroquinoline, tetrahydrothiophene, tetrazole, 1,3-thiazole, thiazolidine, thiomorpholine, thiophene, triazole and triazolone.

The invention furthermore relates to a process for preparing the compound of the formula I and/or a stereoisomeric form of the compound of the formula I and/or a physiologically tolerated salt of the compound of the formula I, which comprises a) reacting a compound of the formula IV

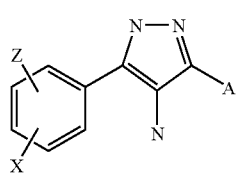

(IV)

with a compound of the formulae Va or Vb

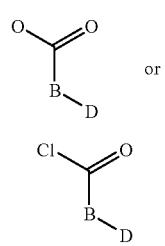

(Va)

or (Vb)

to give a compound of the formula VI

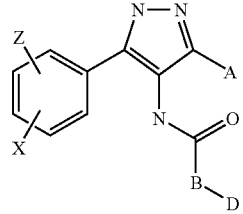

(VI)

and reacting a compound of the formula VI in the presence of phosphorus pentoxide and phosphorus oxychloride to give a protected compound of the formula I and, in conclusion, eliminating the protecting group, b) resolving a compound of the formula I, which has been prepared in accordance with method a) and which, on account of its chemical structure, appears in enantiomeric forms, into the pure enantiomers by means of salt formation with enantiomerically pure acids or bases, chromatography on chiral stationary phases or derivatization using chiral enantiomerically pure compounds, such as amino acids, separating the resulting diastereomers and eliminating the chiral auxiliary groups, or c) either isolating the compound of the formula I, which has been prepared in accordance with methods a) or b), in free form or, when acidic or basic groups are present, converting it into physiologically tolerated salts.

The starting compounds of the formula IV, Va and Vb, and reagents, which are employed can either be prepared using known methods or can be obtained commercially.

The reactions take place, for example, by reacting 3,5-substituted 1H-pyrazol-4-ylamines (compounds of the formula IV) with acids (compounds of the formula Va) in accordance with the carbodiimide method or with acid chlorides (compounds of the formula Vb) to give the corresponding amides (compounds of formula VI) as summarized in Scheme I. These amide forming reactions to form the compound of, formula VI can be carried out using any of the procedures known in the art. Generally, it has been found that use of acid chlorides of formula (Vb) affords the desirable amides. The reaction can generally be carried out in the presence of a suitable organic base such as amine solvent at ambient reaction conditions. Examples of amine solvents include pyridine, triethylamine and the like. In certain instances an additional organic solvent may be used as a cosolvent. Examples of cosolvents include halogenated solvents such as chloroform, methylene chloride and the like. A cosolvent combination of pyridine/methylene chloride or triethylamine/methylene chloride are preferred.

Scheme I

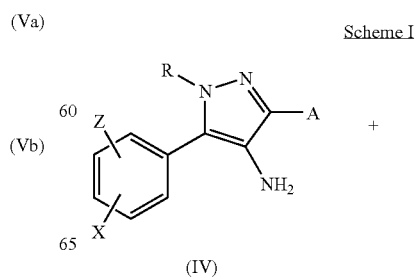

(IV)

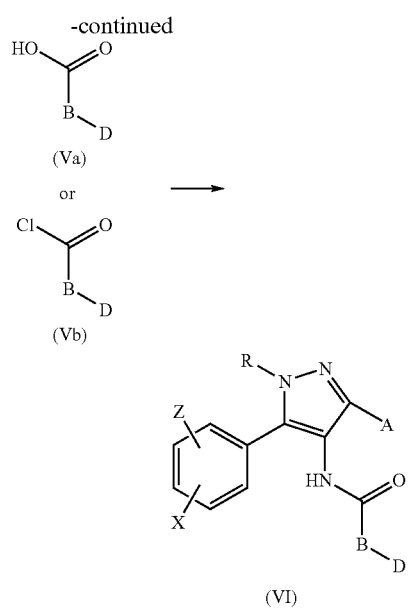

(Va)

or (Vb)

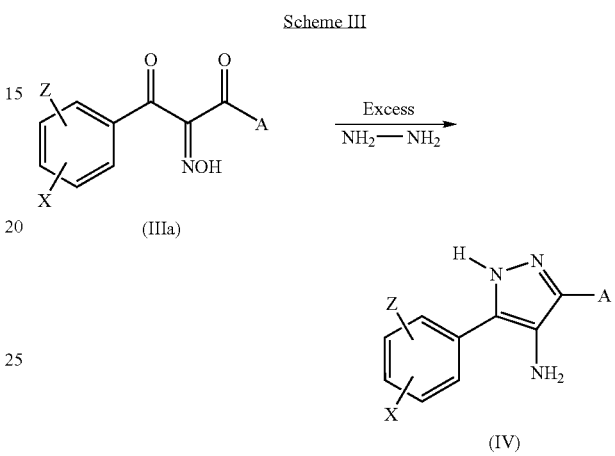

(VI)

The starting compound of the formula (IV) can also be prepared by the steps as depicted in Scheme II. In Step A of Scheme II, the 1,3 diketo compound of the formula (II) is treated with a suitable reagent to form an oxime of the formula (IIIa). Any of the known reaction conditions to carry out such a transformation can be employed for such convertions. For instance, such reactions can be carried out using a nitrite salt such as sodium nitrite in the presence of an acid, e.g., acetic acid (see, J. Fluor. Chem., (1997), 84, p 107).

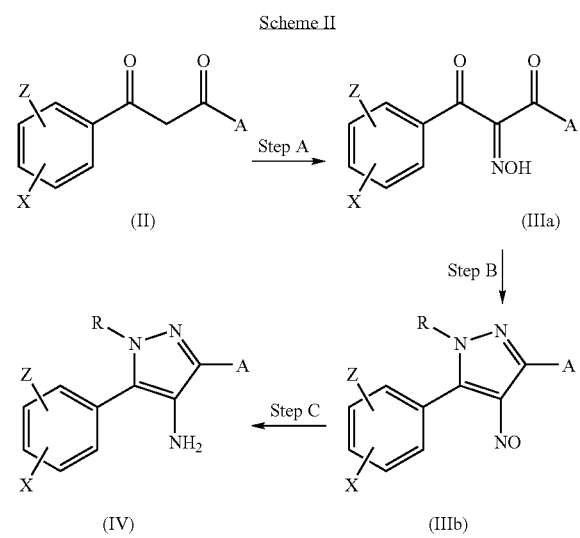

In Step B, Scheme II, the oxime of the formula (IIIa) is further reacted with hydrazine to form a nitroso compound of formula (IIIb) in which R is hydrogen (also see, J. Fluor. Chem., (1997), 84, p 107). The nitroso compound of formula (IIIb) is then hydrogenated to form the starting compound of formula (IV). Any of the known hydrogenation reactions can be employed to reduce the nitroso group to the amino group. Generally, it has been found that catalytic hydrogenation over palladium/carbon affords the compound of formula (IV).

Advantageously, in some instances, it has now been found that use of excess hydrazine in step B of Scheme II directly leads to amino starting compound of formula (IV) as shown in Scheme III. This is particularly advantageous and economical as it eliminates hydrogenation step, step c in Scheme II.

All the protected compounds of formula I can be prepared from compounds of the formula VI in the presence of phosphorus pentoxide and phosphorus oxychloride in boiling xylene. In some instances, the reaction can also be carried out in the absence of any solvent in the presence of phosphorus pentoxide and boiling phosphorus oxychloride. It has also been found that this cyclization step can also be carried out in two steps; first reacting the compound of formula (VI) with phosphorus oxychloride in boiling nitrobenzene and then subsequently reacting the mixture with stannic chloride. This reaction step can also be carried out using any of the other suitable Lewis acids. Protected compounds of the formula I are used as the starting compounds for the deprotection of functional groups and further functionalization.

If it arises in diastereoisomeric or enantiomeric form, and accrues as their mixtures in the chosen synthesis, the compound of the formula I is separated, in process step b), into the pure stereoisomers, either by chromatography on an optionally chiral support material or, if the racemic compound of the formula I is capable of salt formation, by means of fractionally crystallizing the diastereomeric salts which are formed using an optically active base or acid as auxiliary substance. Examples of suitable chiral stationary phases for the thin-layer- or column-chromatographic separation of enantiomers are modified silica gel supports (what are termed Pirkle phases) and high molecular weight carbohydrates such as triacetyl cellulose. For analytical purposes, it is also possible, after appropriate derivatization known to the skilled person, to use gas-chromatographic methods on chiral stationary phases. In order to separate the racemic carboxylic acids into the enantiomers, an optically active, as a rule commercially obtainable, base, such as (−)-nicotine, (+)- and (−)-phenylethylamine, quinine bases, L-lysine or L- and D-arginine, is used to form the differently soluble diastereomeric salts, after which the more difficultly soluble component is isolated as a solid, the more readily soluble diastereomer is separated off from the mother liquor, and the pure enantiomers are isolated from the diastereomeric salts which have been obtained in this way. It is possible, in what is in principle the same manner, to use optically active acids, such as (+)-10-camphorsulfonic acid, D- and L-tartaric acid, D- and L-lactic acid and (+)- and (−)-mandelic acid, to convert the racemic compounds of the formula I which contain a basic group, such as an amino group, into the pure enantiomers. It is also possible to use appropriately activated or optionally N-protected enantiomerically pure amino acids to convert chiral compounds which contain alcohol or amine functions into the corresponding esters or amides or, conversely, to convert chiral carboxylic acids into the amides using carboxy-protected enantiomerically pure amino acids or into the corresponding chiral esters using enantiomer pure hydroxycarboxylic acids such as lactic acid. The chirality of the amino acid or alcohol radical, which has been introduced in enantiomerically pure form, can then be used to separate the isomers by means of separating the diastereomers, which are now present, by means of crystallization or chromatography on suitable stationary phases and, after that, using suitable methods to eliminate the entrained chiral molecule moiety once again.

Acidic or basic products of the compound of the formula I can be present in the form of their salts or in free form. Preference is given to pharmacologically tolerated salts, e.g. alkali metal or alkaline earth metal salts or hydrochlorides, hydrobromides, sulfates, hemisulfates, all the possible phosphates and also salts of the amino acids, of natural bases or carboxylic acids.

Physiologically tolerated salts are prepared in a manner known per se, in accordance with process step c), from the compounds of the formula I, including their stereoisomeric forms, which are capable of salt formation. The compounds of the formula I form stable alkali metal salts, alkaline earth metal salts or optionally substituted ammonium salts with basic reagents such as hydroxides, carbonates, hydrogen carbonates, alkoxides and ammonia or organic bases, for example trimethylamine or triethylamine, ethanolamine or triethanolamine, or else basic amino acids, for example lysine, ornithine or arginine. If the compounds of the formula I possess basic groups, stable acid addition salts can also be prepared using strong acids. Both inorganic and organic acids, such as hydrochloric acid, hydrobromic acid, sulfuric acid, phosphoric acid, methanesulfonic acid, benzenesulfonic acid, p-toluenesulfonic acid, 4-bromobenzenesulfonic acid, cyclohexylamidosulfonic acid, trifluoromethylsulfonic acid, acetic acid, oxalic acid, tartaric acid, succinic acid and trifluoroacetic acid, are suitable for this purpose.

The invention also relates to a pharmaceutical which is characterized by an effective content of at least one compound of the formula I and/or of a physiologically tolerated salt of the compound of the formula I and/or an optionally stereoisomeric form of the compound of the formula I, together with a pharmaceutically suitable and physiologically tolerated carrier substance, additive and/or other active compounds and auxiliary substances.

The present invention also relates to a pharmaceutical composition, comprising at least one compound of the formula I in all its stereoisomeric forms and mixtures thereof in any ratio and/or its physiologically tolerable salts and a pharmaceutically suitable and physiologically tolerated excipient and, where appropriate, other suitable active compounds, additives or auxiliary substances.

On account of their pharmacological properties, the compounds according to the invention are suitable for producing a pharmaceutical for the selective prophylaxis and therapy of all those diseases whose course involves an increased activity of NIK.

The present invention also relates to a method of treating a disease condition associated with the increased activity of NIK comprising administering to a patient suffering from said disease condition a therapeutically effective amount of a compound of formula (I):

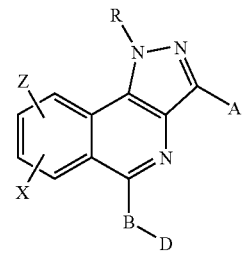

or a stereoisomeric form or a pharmaceutically acceptable salt of the compound of the formula I, wherein A, B, D, X, Z and R are as described herein.

The invention furthermore relates to a method of treating a disease condition as described herein using compounds of one of the embodiments as described hereinabove. In general, the compounds of this invention are suitable for treating a disease condition that is caused due to an inflammatory component.

These diseases include degenerative joint diseases such as osteoarthritis and rheumatoid arthritis. The compounds of the formula I are furthermore suitable for treating asthma and transplantations such as rejection reactions on the part of the body against the transplanted organ and also rejection reactions on the part of the transplanted organ against the body into which the organ has been transplanted. The compounds of formula (I) are also suitable for treating irritable bowel disease, Alzheimer's disease, stroke, diabetes, atherosclerosis and multiple sclerosis.

In an additional aspect of this invention this invention relates to a method of treating a disease condition associated with inflammation comprising administering to a patient suffering from said disease condition a therapeutically effective amount of a compound of formula (I):

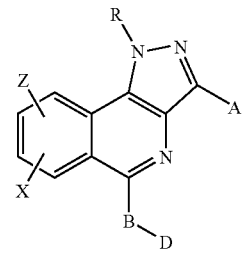

or a stereoisomeric form or a pharmaceutically acceptable salt of the compound of the formula I, wherein
A is —($C_1$–$C_6$)-alkyl, in which alkyl is straight-chain or branched and is optionally substituted, once or more, independently of each other, by
—$OR^1$ or
—C(O)—$OR^1$, —C(O)—NR$^1$R$^1$,
—C(O)—NR$^1$—SO$_2$R$^1$,
—NR$^1$R$^1$,
—CN, in which R$^1$ is
  hydrogen,
  —(C$_1$–C$_6$)-alkyl,
  —(C$_6$–C$_{14}$)aryl or
  fluoroalkyl of the formula —C$_n$H$_x$F$_y$ or fluoroalkoxy of the formula —OC$_n$H$_x$F$_y$, wherein n is an integer from 1 to 6, x is an integer from 0 to 12, y is an integer from 1 to 13 and sum of x and y is 2n+1,
—O—R$^1$,
—SR$^1$,
—S(O)—R$^1$,
—S(O)$_2$—R$^1$,
—C(O)—OR$^1$,
fluoroalkyl of the formula —C$_n$H$_x$F$_y$ or fluoroalkoxy of the formula —OC$_n$H$_x$F$_y$, wherein n is an integer from 1 to 6, x is an integer from 0 to 12, y is an integer from 1 to 13 and sum of x and y is 2n+1,
—C(O)—NR$^1$R$^1$,
—C(O)—NR$^1$—SO$_2$R$^1$,
—NR$^1$R$^1$,
—CN,
heteroaryl having from 5 to 14 ring members, in which heteroaryl is unsubstituted or optionally substituted once or more, independently of each other, by R$^2$, in which R$^2$ is
  —(C$_1$–C$_4$)-alkyl,
  —OH,
  —O—(C$_1$–C$_4$)-alkyl,
  halogen,
  —N(R$^3$)—R$^4$, in which R$^3$ and R$^4$ are, independently of each other, hydrogen atom or —(C$_1$–C$_4$)-alkyl,
  fluoroalkyl of the formula —C$_n$H$_x$F$_y$ or fluoroalkoxy of the formula —OC$_n$H$_x$F$_y$, wherein n is an integer from 1 to 4, x is an integer from 0 to 8, y is an integer from 1 to 9 and sum of x and y is 2n+1,
  —CN
  —SR$^1$,
  —S(O)—R$^1$,
  —S(O)$_2$—R$^1$ or
  —C(O)—NR$^1$R$^1$,
—(C$_3$–C$_6$)-cycloalkyl, in which cycloalkyl is unsubstituted or substituted, once or more, independently of each other, by R$^2$, and R$^2$ is defined as above,
heterocycle having from 5 to 12 ring members, in which heterocycle is unsubstituted or substituted, once or more, independently of each other, by R$^2$ and R$^2$ is defined as above,
B is a covalent bond,
  —C=CR$^1$—,
  —C≡C—,
  —O(CH$_2$)$_a$—, in which a is an integer from 1 to 4,
  O, S, NR$^2$, —C(O)—, —NR$^2$—C(O)—, —C(O)—NR$^2$—, —NR$^2$—SO$_2$—, —SO$_2$—NR$^2$—, —NR$^2$—C(O)—NR$^2$—, and R$^2$ is defined as above, or
  —(C$_1$–C$_4$)-alkylene, in which alkylene is straight-chain or branched and is optionally substituted, once or more, independently of each other, by R$^1$, and R$^1$ is defined as above,
D is —(C$_1$–C$_6$)-alkyl, in which alkyl is straight-chain or branched and is optionally substituted, once or more, independently of each other, by R$^1$, and R$^1$ is defined as above, heteroaryl having from 5 to 14 ring members, in which heteroaryl is unsubstituted or is substituted once or more, independently of each other, by R$^2$ and R$^2$ is defined as above,
heterocycle having from 5 to 12 ring members, in which heterocycle is unsubstituted or substituted, once or more, independently of each other, by R$^2$ and R$^2$ is defined as above,
—(C$_6$–C$_{14}$)-aryl, in which aryl is unsubstituted or substituted, once or more, independently of each other, by R$^2$ and R$^2$ is defined as above, or
—(C$_3$–C$_6$)-cycloalkyl, in which cycloalkyl is unsubstituted or substituted, once or more, independently of each other, by R$^2$ and R$^2$ is defined as above, or
B-D is hydrogen,
  halogen,
  fluoroalkyl of the formula —C$_n$H$_x$F$_y$ or fluoroalkoxy of the formula —OC$_n$H$_x$F$_y$, wherein n is an integer from 1 to 4, x is an integer from 0 to 8, y is an integer from 1 to 9 and sum of x and y is 2n+1,
  —(CH$_2$)$_a$—Y—R$^3$, in which a is an integer from 1 to 4, Y is O, S, NR$^2$, and R$^3$ is
    —(C$_1$–C$_6$)-alkyl,
    —(C$_6$–C$_{14}$)-aryl,
    —(C$_3$–C$_6$)-cycloalkyl, and
R is hydrogen,
  —(C$_1$–C$_6$)-alkyl, or
  —(C$_6$–C$_{14}$)-aryl-(C$_1$–C$_6$)-alkyl, in which aryl is unsubstituted or substituted, once or more, independently of each other, by R$^2$, and R$^2$ is defined as above, and
X and Z are identical or different and are, independently of each other selected from:
  hydrogen atom,
  —(C$_1$–C$_4$)-alkyl,
  —OH,
  —O—(C$_1$–C$_4$-alkyl),
  halogen,
  fluoroalkyl of the formula —C$_n$H$_x$F$_y$ or fluoroalkoxy of the formula —OC$_n$H$_x$F$_y$, wherein n is an integer from 1 to 6, x is an integer from 0 to 12, y is an integer from 1 to 13 and sum of x and y is 2n+1,
  —C(O)—OR$^1$,
  —C(O)—NR$^1$R$^1$,
  —C(O)—NR$^1$—SO$_2$R$^1$,
  —NR$^1$R$^1$,
  —NR$^1$—C(O)—NR$^1$R$^1$,
  —NR$^1$—C(O)—R$^1$,
  —NR$^1$—C(O)—OR$^1$,
  —O—C(O)—NR$^1$R$^1$,
  —CN,
  —SR$^1$,
  —S(O)—R$^1$,
  —S(O)$_2$—R$^1$,
  —S(O)$_2$—NR$^1$R$^1$,
  —NR$^1$—SO$_2$—R$^1$, in which R$^1$ is as defined above,
  heterocycle having from 5 to 12 ring members, in which heterocycle is unsubstituted or substituted, once or more, independently of each other, by R$^2$, and R$^2$ is defined as above, or
  —(C$_3$–C$_6$)-cycloalkyl, in which cycloalkyl is unsubstituted or substituted, once or more, independently of each other, by R$^2$, and R$^2$ is defined as above.
In further aspect of this method of the present invention the compound is having the following substituents:
A is —(C$_1$–C$_3$)-alkyl, in which alkyl is straight-chain or branched and is optionally substituted, once or more, independently of each other, by —O—R¹, or
—C(O)—OR¹, in which R¹ is
  hydrogen,
  —($C_1$–$C_3$)-alkyl, or
  —$CF_3$
fluoroalkyl of the formula —$C_nH_xF_y$, or fluoroalkoxy of the formula —$OC_nH_xF_y$, wherein n is an integer from 1 to 3, x is an integer from 0 to 6, y is an integer from 1 to 7 and sum of x and y is 2n+1,
B is a covalent bond or O,
D is phenyl or naphthyl, in which phenyl or naphthyl is unsubstituted or substituted, once or more, independently of each other, by $R^2$, in which $R^2$ is
  fluorine, chlorine or bromine,
  —OH,
  —$CF_3$,
  —$SR^1$, in which $R^1$ is defined as above,
  —($C_1$–$C_4$)-alkyl
  —O—($C_1$–$C_2$)-alkyl or
  —N($R^3$)—$R^4$, in which $R^3$ and $R^4$ are, independently of each other, hydrogen atom or —($C_1$–$C_3$)-alkyl,
  heteroaryl selected from the group consisting of pyridyl, furanyl, pyrrolyl, isoxazolyl, benzofuranyl, benzothiophenyl, quinolinyl, isoquinolinyl, quinoxalinyl and thiophenyl, in which heteroaryl is unsubstituted or substituted, once or more, independently of each other, by $R^2$ in which $R^2$ is defined as above, or
  —($C_4$–$C_6$)-cycloalkyl, in which cycloalkyl is unsubstituted or substituted, once or more, independently of each other, by $R^2$ and $R^2$ is defined as above, or
B-D is (($CH_2$)$_a$—Y—$R^3$, in which a is an integer from 1 to 2, Y is O and $R^3$ is —($C_1$–$C_3$)-alkyl, and
R is hydrogen,
  —($C_1$–$C_3$)-alkyl, or
  -phenyl-($C_1$–$C_3$)-alkyl, and
X and Z are identical or different and are, independently of each other, hydrogen, —C(O)—O($C_1$–$C_3$)alkyl, —$OCH_3$, —N($CH_3$)$_2$ or halogen.

In practice of this aspect of the method of this invention all of the specific compounds as listed hereinabove can be employed.

The various disease conditions as listed hereinabove can be treated with this aspect of the method of this invention. More specifically the disease conditions that can be treated without any limitations are multiple sclerosis, atheroslerosis, inflammatory bowel disease, Alzheimer's disease, stroke and diabetes.

The pharmaceuticals according to the invention can be administered orally, by inhalation, rectally or transdermally or by means of subcutaneous, intraarticular, intraperitoneal or intravenous injection. Oral administration is preferred.

The invention also relates to a process for producing a pharmaceutical which comprises bringing at least one compound of the formula I, together with a pharmaceutically suitable and physiologically tolerated excipient and, where appropriate, other suitable active compounds, additives or auxiliary substances, into a suitable form for administration.

Examples of suitable solid or galenic preparation forms are granules, powders, sugar-coated tablets, tablets, (micro) capsules, suppositories, syrups, juices, suspensions, emulsions, drops or injectable solutions, and also preparations with protracted active compound release, in the preparation of which customary auxiliary substances, such as carrier substances, disintegrants, binders, coating agents, swelling agents, glidants or lubricants, flavorings, sweeteners and solubilizers are used. Frequently employed auxiliary substances which may be mentioned are magnesium carbonate, titanium dioxide, lactose, mannitol and other sugars, talc, milk protein, gelatin, starch, cellulose and its derivatives, animal and vegetable oils, such as cod liver oil, sunflower oil, groundnut oil or sesame oil, polyethylene glycol and solvents, such as sterile water and monohydric or polyhydric alcohols, such as glycerol.

The pharmaceutical preparations are preferably produced and administered in dosage units, with each unit containing as the active constituent, a particular dose of the compound of the formula II according to the invention. In the case of solid dosage units, such as tablets, capsules, sugar-coated tablets or suppositories, this dose can be up to about 1000 mg, preferably from about 50 mg to 300 mg, and, in the case of injection solutions in ampoule form, up to about 300 mg, preferably from about 10 mg to 100 mg.

Depending on the activity of the compound according to the formula II, daily doses of from about 20 mg to 1000 mg of active compound, preferably of from about 100 mg to 500 mg, are indicated for treating an adult patient of about 70 kg in weight. However, higher or lower daily doses may also possibly be appropriate. The daily dose can be administered either by means of a once-only administration in the form of a single dosage unit, or of several smaller dosage units, or by means of the multiple administration of subdivided doses at predetermined intervals.

As a rule, mass-spectroscopic methods (FAB-MS, ESI-MS) are used for determining end products, the main peak being given in each case. Temperatures are given in degrees centigrade; RT denotes room temperature (from 22° C. to 26° C.). Abbreviations which are used are either explained or correspond to the customary conventions.

The invention is explained in more detail below with the aid of examples.

PREPARATION EXAMPLES

In general the compounds of this invention as prepared below were characterized by High Pressure Liquid Chromatograph (HPLC) using one of the following three methods:

Method A: HPLC was run on Synergi 2U Hydro-RP 20×4.0 MM COL, water (0.1% trifluoroacetic acid/acetonitrile (0.1% trifluoroacetic acid)=10/90→90/10).

Method B: Agilent 1100 Series LC/MSD YMC Pro $C_{18}$ S5 120A 4.6×30 MM Col, Waterf (0.1% trifluoroacetic acid/acetonitrile (0.1% trifluoroacetic acid)=95/5→5/95), run time 5 min.

Mass S[ectra were run as follows:
Method A: Micromass LCT-TOF MS, Scan M/Z 100-1000.
Method B: Micromass LCZ-TOF MS, Scan M/Z 100-800.

Example 1

3,5-Diphenyl-1H-pyrazolo[4,3-c]isoquinoline (1)

a) N-(3,5-diphenyl-1H-pyrazol-4-yl)benzylamine (2)

574 mg of hydroxybenzotriazole and 822 μl of diisopropylcarbodiimide were added to a solution of 260 mg of benzoic acid in 10 ml of methylene chloride, after which 500 mg of 3,5-diphenyl-1H-pyrazol-4-ylamine in 2 ml of acetonitrile were added dropwise, at 0° C.; the mixture was then stirred at room temperature (RT) for 12 hours (h), after which water was added and the whole was extracted with ethyl acetate. The organic phase was dried over magnesium sulfate and concentrated under reduced pressure. The residue contained the title compound and was used in the following reaction without further purification.

b) 3,5-Diphenyl-1H-pyrazolo[4,3-c]isoquinoline (1)

201 mg of phosphorus pentoxide were added to a solution of 240 mg of N-(3,5-diphenyl-1H-pyrazol-4-yl)benzylamine (2) in 10 ml of xylene, after which 195 µl of phosphorus oxychloride were added dropwise at 150° C. The reaction solution was stirred at 150° C. for 4 h and then stirred at RT for 12 h; a saturated solution of sodium hydrogen carbonate was then added and the whole was extracted with methylene chloride. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained:

1. $C_{22}H_{15}N_3$ (321.38); MS (ESI) 322 (M+H)

Example 2

5-(3-Methoxyphenyl)-3-methyl-1H-pyrazolo[4,3-c]isoquinoline (3)

a) 3-Methoxy-N-(3-methyl-5-phenyl-1H-pyrazol-4-yl)benzamide (4)

311 mg of hydroxybenzotriazole and 445 µl of diisopropylcarbodiimide were added to a solution of 160 mg of 3-methoxybenzoic acid in 10 ml of dimethylformamide, after which 200 mg of 3-methyl-5-phenyl-1H-pyrazol-4-ylamine were added; the mixture was then stirred at RT for 12 h, after which water was added and the whole was extracted with methylene chloride. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 4 $C_{17}H_{15}N_3O_2$ (293.33); MS (ESI) 294 (M+H).

b) 5-(3-Methoxyphenyl)-3-methyl-1H-pyrazolo[4,3-c]isoquinoline (3)

128 mg of 3-methoxy-N-(3-methyl-5-phenyl-1H-pyrazol-4-yl)benzamide (4) were suspended in 5 ml of xylene and the suspension was boiled at 160° C.; 119 mg of phosphorus pentoxide were then added and the mixture was subsequently stirred at 160° C. for 15 min. 27 µl of phosphorus oxychloride were added dropwise to the suspension, which was then stirred at 160° C. for 12 h; a saturated solution of sodium hydrogen carbonate was then added and the whole was extracted with ethyl acetate. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 3.

$C_{18}H_{15}N_3O$ (298.34); MS (ESI 290 (M+H)

Example 3

3-(3-Methyl-1H-pyrazolo[4,3-c]isoquinolin-5-yl)phenol (5)

380 µl of 1M boron tribromide solution in methylene chloride were added dropwise, at −78° C., to a solution of 55 mg of 5-(3-methoxyphenyl)-3-methyl-1H-pyrazolo[4,3-c]isoquinoline (3) in 3 ml of methylene chloride. The reaction solution was stirred at RT for 12 h, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 5.

$C_{17}H_{13}N_3O$ (275.31); MS (ESI 276 (M+H)

Example 4

5-(2-Methoxyphenyl)-3-methyl-1H-pyrazolo[4,3-c]isoquinoline (6)

a) 2-Methoxy-N-(3-methyl-5-phenyl-1H-pyrazol-4-yl)benzamide (7)

The preparation took place in analogy with Example 2a), starting with 175 mg of 2-methoxybenzoic acid. The following was obtained: 7.

$C_{18}H_{17}N_3O_2$ (307.36); MS (ESI) 308 (M+H)

b) 5-(2-Methoxyphenyl)-3-methyl-1H-pyrazolo[4,3-c]isoquinoline (6)

The preparation took place in analogy with Example 1b), starting with 90 mg of 2-methoxy-N-(3-methyl-5-phenyl-1H-pyrazol-4-yl)benzamide (7). The following was obtained: 6.

$C_{18}H_{15}N_3O_2$ (289.34); MS (ESI) 290 (M+H)

Example 5

5-(2,3-Dimethoxyphenyl)-3-methyl-1H-pyrazolo[4,3-c]isoquinoline (8)

a) 2,3-Dimethxoy-N-(3-methyl-5-phenyl-1H-pyrazol-4-yl)benzamide (9)

The preparation took place in analogy with Example 2a), starting with 210 mg of 2,3-dimethoxybenzoic acid. The following was obtained: 9.

$C_{19}H_{19}N_3O_3$ (337.38); MS (ESI 338)(M+H)

b) 5-(2,3-Dimethoxyphenyl)-3-methyl-1H-pyrazolo[4,3-c]isoquinoline (8)

The preparation took place in analogy with Example 1b), starting with 40 mg of 2,3-dimethoxy-N-(3-methyl-5-phenyl-1H-pyrazol-4-yl)benzamide (9). The following was obtained: 8. $C_{19}H_{17}N_3O_2$ (319.37);

MS (ESI) 320 (M+H)

Example 6

5-(2,4-Dimethoxyphenyl)-3-methyl-1H-pyrazolo[4,3-c]isoquinoline (10)

a) 2,4-Dimethoxy-N-(3-methyl-5-phenyl-1H-pyrazol-4-yl)benzamide (11)

The preparation took place in analogy with Example 2a), starting with 210 mg of 2,4-dimethoxybenzoic acid. The following was obtained:

11. $C_{19}H_{19}N_3O_3$ (337.38); MS (ESI) 338 (M+H)

b) 5-(2,4-Dimethoxyphenyl)-3-methyl-1H-pyrazolo[4,3-c]isoquinoline (10)

The preparation took place in analogy with Example 1b), starting with 87 mg of 2,4-dimethoxy-N-(3-methyl-5-phe nyl-1H-pyrazol-4-yl)benzamide (11). The following was obtained: 10.

$C_{19}H_{17}N_3O_2$ (319.37); MS (ESI) 320 (M+H)

Example 7

5-(2,6-Dimethoxyphenyl)-3-methyl-1H-pyrazolo[4,3-c]isoquinoline (12)

a) 2,6-Dimethoxy-N-(3-methyl-5-phenyl-1H-pyrazol-4-yl)benzamide (13)

The preparation took place in analogy with Example 2a), starting with 210 mg of 2,6-dimethoxybenzoic acid. The following was obtained: 13.

$C_{19}H_{19}N_3O_3$ (337.38); MS (ESI) 338 (M+H)

b) 5-(2,6-Dimethoxyphenyl)-3-methyl-1H-pyrazolo[4,3-c]isoquinoline (12)

The preparation took place in analogy with Example 1b), starting with 100 mg of 2,6-dimethoxy-N-(3-methyl-5-phenyl-1H-pyrazol-4-yl)benzamide (13). The following was obtained: 12. $C_{19}H_{17}N_3O_2$ (319.37); MS (ESI 320) (M+H)

Example 8

5-(3,4-Dimethoxyphenyl)-3-methyl-1H-pyrazolo[4,3-c]isoquinoline (14)

a) 3,4-Dimethoxy-N-(3-methyl-5-phenyl-1H-pyrazol-4-yl)benzamide (15)

The preparation took place in analogy with Example 2a), starting with 210 mg of 3,4-dimethoxybenzoic acid. The following was obtained:

15. $C_{19}H_{19}N_3O_3$ (337.38); MS (ESI) 338 (M+H)

b) 5-(3,4-Dimethoxyphenyl)-3-methyl-1H-pyrazolo[4,3-c]isoquinoline (14)

The preparation took place in analogy with Example 1b), starting with 100 mg of 3,4-dimethoxy-N-(3-methyl-5-phenyl-1H-pyrazol-4-yl)benzamide (15). The following was obtained: 14. $C_{19}H_{17}N_3O_2$ (319.37); MS (ESI) 320 (M+H)

Example 9

5-(3,5-Dimethoxyphenyl)-3-methyl-1H-pyrazolo[4,3-c]isoquinoline (16)

a) 3,5-Dimethoxy-N-(3-methyl-5-phenyl-1H-pyrazol-4-yl)benzamide (17)

The preparation took place in analogy with Example 2a), starting with 210 mg of 3,5-dimethoxybenzoic acid. The following was obtained:

17. $C_{19}H_{19}N_3O_3$ (337.38); MS (ESI) 338 (M+H)

b) 5-(3,5-Dimethoxyphenyl)-3-methyl-1H-pyrazolo[4,3-c]isoquinoline (16)

The preparation took place in analogy with Example 1b), starting with 60 mg of 3,5-dimethoxy-N-(3-methyl-5-phenyl-1H-pyrazol-4-yl)benzamide (17). The following was obtained: 16. $C_{19}H_{17}N_3O_2$ (319.37); MS (ESI) 320 (M+H)

Example 10

5-(2,3,4-Trimethoxyphenyl)-3-methyl-1H-pyrazolo[4,3-c]isoquinoline (18)

a) 2,3,4-Trimethoxy-N-(3-methyl-5-phenyl-1H-pyrazol-4-yl)benzamide (19)

The preparation took place in analogy with Example 2a), starting with 244 mg of 2,3,4-trimethoxybenzoic acid. The following was obtained:

19. $C_{20}H_{21}N_3O_4$ (367.41); MS (ESI) 368 (M+H)

b) 5-(2,3,4-Trimethoxyphenyl)-3-methyl-1H-pyrazolo[4,3-c]isoquinoline (18)

The preparation took place in analogy with Example 1b), starting with 73 mg of 2,3,4-trimethoxy-N-(3-methyl-5-phenyl-1H-pyrazol-4-yl)benzamide (19). The following was obtained: 18. $C_{20}H_{19}N_3O_3$ (349.39) MS (ESI) 350 (M+H)

Example 11

5-(2,4,6-Trimethoxyphenyl)-3-methyl-1H-pyrazolo[4,3-c]isoquinoline (20)

a) 2,4,6-Trimethoxy-N-(3-methyl-5-phenyl-1H-pyrazol-4-yl)benzamide (21)

The preparation took place in analogy with Example 2a), starting with 244 mg of 2,4,6-trimethoxybenzoic acid. The following was obtained:

21. $C_{20}H_{21}N_3O_4$ (367.41); MS (ESI) 368 (M+H)

b) 5-(2,4,6-Trimethoxyphenyl)-3-methyl-1H-pyrazolo[4,3-c]isoquinoline (18)

The preparation took place in analogy with Example 1b), starting with 63 mg of 2,4,6-trimethoxy-N-(3-methyl-5-phenyl-1H-pyrazol-4-yl)benzamide (21). The following was obtained: 20. $C_{20}H_{19}N_3O_3$ (349.39);

MS (ESI) 350 (M+H)

Example 12

5-(3,4,5-Trimethoxyphenyl)-3-methyl-1H-pyrazolo[4,3-c]isoquinoline (22)

a) 3,4,5-Trimethoxy-N-(3-methyl-5-phenyl-1H-pyrazol-4-yl)benzamide (23)

The preparation took place in analogy with Example 2a), starting with 244 mg of 3,4,5-trimethoxybenzoic acid. The following was obtained:

23. $C_{20}H_{21}N_3O_4$ (367.41); MS (ESI) 368 (M+H)

b) 5-(3,4,5-Trimethoxyphenyl)-3-methyl-1H-pyrazolo[4,3-c]isoquinoline (22)

The preparation took place in analogy with Example 2b), starting with 65 mg of 3,4,5-trimethoxy-N-(3-methyl-5-phenyl-1H-pyrazol-4-yl)benzamide (23). The following was obtained: 22. $C_2H_{19}N_3O_3$ (349.39);

MS (ESI) 350 (M+H)

Example 13

5-(2-Ethoxyphenyl)-3-methyl-1H-pyrazolo[4,3-c]isoquinoline (24)

a) 2-Ethoxy-N-(3-methyl-5-phenyl-1H-pyrazol-4-yl)benzamide (25)

The preparation took place in analogy with Example 2a), starting with 191 mg of 2-ethoxybenzoic acid. The following was obtained: 25.

$C_{19}H_{19}N_3O_2$ (321.389); MS (ESI) 322 (M+H)

b) 5-(2-Ethoxyphenyl)-3-methyl-1H-pyrazolo[4,3-c]isoquinoline (24)

The preparation took place in analogy with Example 1b), starting with 60 mg of 2-ethoxy-N-(3-methyl-5-phenyl-1H-pyrazol-4-yl)benzamide (25). The following was obtained: 24. $C_{19}H_{17}N_3O$ (303.37);

MS (ESI) 304 (M+H)

Example 14

5-(4-Diethylaminophenyl)-3-methyl-1H-pyrazolo[4,3-c]isoquinoline (26)

a) 4-Diethylamino-N-(3-methyl-5-phenyl-1H-pyrazol-4-yl)benzamide (27)

The preparation took place in analogy with Example 2a), starting with 222 mg of 4-diethylaminobenzoic acid. The following was obtained:

27. $C_{21}H_{24}N_4O$ (348.45); MS (ESI) 349 (M+H)

b) 5-(4-Diethylaminophenyl)-3-methyl-1H-pyrazolo[4,3-c]isoquinoline (26)

The preparation took place in analogy with Example 1b), starting with 130 mg of 4-diethylamino-N-(3-methyl-5-phenyl-1H-pyrazol-4-yl)benzamide (27). The following was obtained: 26. $C_{21}H_{22}N_4$ (330.44);

MS (ESI) 331 (M+H)

Example 15

3-Methyl-5-pyridin-4-yl-1H-pyrazolo[4,3-c]isoquinoline (28)

a) N-(3-Methyl-5-phenyl-1H-pyrazol-4-yl)isonicotinamide (29)

205 mg of isonicotinoyl chloride*HCl were added to a solution of 200 mg of 3-methyl-5-phenyl-1H-pyrazol-4-ylamine in 2 ml of pyridine and the mixture was then stirred at RT for 12 h; water was then added and the whole was extracted with methylene chloride. The organic phase was dried over magnesium sulfate, concentrated under reduced pressure and purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 27. $C_{16}H_{14}N_4O$ (278.32); MS (ESI) 279 (M+H)

b) 3-Methyl-5-pyridin-4-yl-1H-pyrazolo[4,3-c]isoquinoline (28)

The preparation took place in analogy with Example 1b), starting with 110 mg of N-(3-methyl-5-phenyl-1H-pyrazol-4-yl)isonicotinamide (29). The following was obtained: 28. $C_{16}H_{12}N_4$ (260.30); MS (ESI) 261 (M+H)

Example 16

3-Methyl-5-pyridin-3-yl-1H-pyrazolo[4,3-c]isoquinoline (30)

a) N-(3-Methyl-5-phenyl-1H-pyrazol-4-yl)nicotinamide (31)

The preparation took place in analogy with Example 15a), starting with 205 mg of nicotinoyl chloride*HCl. The following was obtained: 31. $C_{16}H_{14}N_4O$ (278.32); MS (ESI) 279 (M+H)

b) 3-Methyl-5-pyridin-3-yl-1H-pyrazolo[4,3-c]isoquinoline (30)

The preparation took place in analogy With Example 1b), starting with 140 mg of N-(3-methyl-5-phenyl-1H-pyrazol-4-yl)nicotinamide (31). The following was obtained: 30. $C_{16}H_{12}N_4$ (260.30); MS (ESI) 261 (M+H)

Example 16A

3-Methyl-5-pyridin-3-yl-1H-pyrazolo[4,3-c]isoquinoline (30)

The title compound was also prepared by a modified procedure as described herein.

a) Pyridine-2-carboxylic acid (3-methyl-5-phenyl-1H-pyrazol-4-yl)-amide (C1).

The preparation took place in analogy to Example 33 (B1) starting with 1.207 g picolinoyl chloride hydrochloride, except the product was purified using MPLC (12 g $SiO_2$, 45% ethyl acetate:heptane) to give the title compound as a light tan, amorphous solid.

HPLC $R_T$=2.33 min.

$C_{16}H_{14}N_4O$ (278.32) MS (ESI, method A) 279 (M+H).

b) 3-Methyl-5-pyridin-2-yl-1H-pyrazolo[4,3-c]isoquinoline (C).

The preparation took place in analogy to Example 33 (B) starting with 1.349 g of pyridine-2-carboxylic acid (3-methyl-5-phenyl-1H-pyrazol-4-yl)-amide. The title compound was obtained as a tan solid.

HPLC $R_T$=2.05 min.

$C_{16}H_{12}N_4$ (260.30) MS (ESI, method A) 261 (M+H).

Example 17

3-Methyl-5-pyridin-2-yl-1H-pyrazolo[4,3-c]isoquinoline (32)

a) N-(3-methyl-5-phenyl-1H-pyrazol-4-yl)-pyridine-2-carboxamide (33)

The preparation took place in analogy with Example 15a), starting with 205 mg of pyridine-2-carbonyl chloride*HCl. The following was obtained: 33. $C_{16}H_{14}N_4O$ (278.32); MS (ESI) 279 (M+H)

b) 3-Methyl-5-pyridin-2-yl-1H-pyrazolo[4,3-c]isoquinoline (32)

The preparation took place in analogy with Example 1b), starting with 110 mg of N-(3-methyl-5-phenyl-1H-pyrazol-4-yl)-pyridine-2-carboxamide (33). The following was obtained: 32.

$C_{16}H_{12}N_4$ (260.30); MS (ESI) 261 (M+H)

Example 18

5-Benzyl-3-methyl-1H-pyrazolo[4,3-c]isoquinoline (34)

a) N-(3-Methyl-5-phenyl-1H-pyrazol-4-yl)-2-phenylacetamide (35)

The preparation took place in analogy with Example 15a), starting with 152 μl of phenylacetyl chloride. The following was obtained: 35.

$C_{18}H_{17}N_3O$ (291.36); MS (ESI) 292 (M+H)

b) 5-Benzyl-3-methyl-1H-pyrazolo[4,3-c]isoquinoline (34)

The preparation took place in analogy with Example 1b), using 50 mg of N-(3-methyl-5-phenyl-1H-pyrazol-4-yl)-2-phenylacetamide (35). The following was obtained: 34. $C_{18}H_{15}N_3$ (273.34); MS (ESI) 274 (M+H)

Example 19

3-Methyl-5-phenethyl-1H-pyrazolo[4,3-c]isoquinoline (36)

a) N-(3-Methyl-5-phenyl-1H-pyrazol-4-yl)-3-phenylpropionamide (37)

The preparation took place in analogy with Example 15a), starting with 172 μl of 3-phenylpropionyl chloride. The following was obtained: 37.

$C_{19}H_{19}N_3O$ (305.38); MS (ESI) 306 (M+H)

b) 3-Methyl-5-phenethyl-1H-pyrazolo[4,3-c]isoquinoline (36)

The preparation took place in analogy with Example 1b), starting with 110 mg of N-(3-methyl-5-phenyl-1H-pyrazol-4-yl)-3-phenylpropionamide (37). The following was obtained: 36.

$C_{18}H_{15}N_3$ (287.37); MS (ESI) 288 (M+H)

Example 20

3-Methyl-5-(1-methylpiperidin-4-yl)-1H-pyrazolo[4,3-c]isoquinoline (38)

a) N-(3-Methyl-5-phenyl-1H-pyrazol-4-yl)-1-methylpiperidine-4-carboxamide (39)

The preparation took place in analogy with Example 2a), starting with 207 mg of 1-methylpiperidine-4-carboxylic acid*HCl and 197 μl of diisopropylethylamine. The following was obtained: 39.

$C_{17}H_{22}N_4O$ (298.39); MS (ESI) 299 (M+H)

b) 3-Methyl-5-(1-methylpiperidin-4-yl)-1H-pyrazolo[4,3-c]isoquinoline (38)

The preparation took place in analogy with Example 1b), starting with 220 mg of N-(3-methyl-5-phenyl-1H-pyrazol-4-yl)-1-methylpiperidine-4-carboxamide (39). The following was obtained: 38.

$C_{17}H_{20}N_4$ (280.38); MS (ESI) 281 (M+H)

Example 21

7,8-Dimethoxy-3-methyl-5-phenyl-1H-pyrazolo[4,3-c]isoquinoline (40)

a) 1-(3,4-Dimethoxyphenyl)butane-1,3-dione (41)

3.9 g of sodium hydride were initially introduced into 150 ml of cyclohexane, and a solution of 15 g of 1-(3,4-dimethoxyphenyl)ethanone in 16.3 ml of ethyl acetate was added. The reaction solution was boiled at 80° C. for 1 h, after which acetic acid was added and the whole was extracted with MTB-ether. The MTB-ether phase was dried over magnesium sulfate and subjected to rotary evaporation. The residue was chromatographed through silica gel (ethyl acetate/heptane 1/6). The following was obtained: 41 $C_{12}H_{14}O_4$ (222.24); MS (ESI) 223 (M+H)

b) 1-(3,4-Dimethoxyphenyl)butane-1,2,3-trione 2-oxime (42)

5 g of 1-(3,4-dimethoxyphenyl)butane-1,3-dione (41) were initially introduced into 25 ml of acetic acid, and. 1.71 g of sodium nitrite, dissolved in 5 ml of water, were then added dropwise at 15° C. The reaction solution was stirred at RT for 1 h and then remained standing for 2 h. 50 g of ice were added to the solution and the whole was then stored at 0° C. for 12 h, in connection with which the product precipitated out. The product was subsequently filtered off with suction and dried at 50° C. in a drying oven. The following was obtained: 42 $C_{12}H_{13}NO_5$ (251.24); MS (ESI) 252 (M+H)

c) 5-(3,4-Dimethoxyphenyl)-3-methyl-4-nitro-1H-pyrazole (43)

6.77 g of 1-(3,4-dimethoxyphenyl)butane-1,2,3-trione 2-oxime (42) were dissolved in 54 ml of acetic acid, after which 0.96 g of hydrazine was added dropwise at RT and the mixture was subsequently stirred at 60° C. for 2 h. Ice was added to the reaction solution, which was then neutralized with sodium carbonate and extracted with MTB-ether. The organic phase was dried over magnesium sulfate and subjected to rotary evaporation. The following was obtained: 43. $C_{12}H_{13}N_3O_3$ (247.26); MS (ESI) 248 (M+H)

d) 5-(3,4-Dimethoxyphenyl)-3-methyl-1H-pyrazol-4-ylamine (44)

4.84 g of 5-(3,4-dimethoxyphenyl)-3-methyl-4-nitro-1H-pyrazole (43) were dissolved in 80 ml of ethanol, and 0.5 g of Pd/C was added to this solution. The solution was shaken under hydrogen for 2 h, then filtered through magnesium sulfate and subjected to rotary evaporation. The residue was chromatographed through silica gel (ethyl acetate/heptane 3/1). The following was obtained: 44 $C_{12}H_{15}N_3O_2$ (233.27); MS (ESI) 234 (M+H)

e) N-[5-(3,4-Dimethoxyphenyl)-3-methyl-1H-pyrazol-4-yl]benzamide (45)

The preparation took place in analogy with Example 15a), starting with 500 mg of 5-(3,4-dimethoxyphenyl)-3-methyl-1H-pyrazol-4-ylamine (44) and 280 μl of benzoyl chloride. The following was obtained: 45

$C_{19}H_{19}N_3O_3$ (337.38); MS (ESI) 338 (M+H)

f) 7,8-Dimethoxy-3-methyl-5-phenyl-1H-pyrazolo[4,3-c]isoquinoline (40)

The preparation place in analogy with Example 1b), starting with 187 mg of N-[5-(3,4-dimethoxyphenyl)-3-methyl-1H-pyrazol-4-yl]benzamide (45). The following was obtained: 40

$C_{19}H_{17}N_3O_2$ (319.37), MS (ESI) 320 (M+H)

Example 22

7-Methoxy-3-methyl-5-phenyl-1H-pyrazolo[4,3-c]isoquinoline (46)

a) 1-(4-Methoxyphenyl)butane-1,3-dione (47)

The preparation took place in analogy with Example 21a), starting with 15 g of 1-(4-methoxyphenyl)ethanone. The following was obtained: 47

$C_{11}H_{12}O_3$ (192.22); MS (ESI) 193 (M+H)

b) 1-(4-Methoxyphenyl)butane-1,2,3-trione 2-oxime (48)

The preparation took place in analogy with Example 21b), starting with 5 g of 1-(4-methoxyphenyl)butane-1,3-dione (47). The following was obtained: 48 $C_{11}H_{11}NO_4$ (221.21) MS (ESI) 222 (M+H)

c) 5-(4-Methoxyphenyl)-3-methyl-4-nitroso-1H-pyrazole (49)

The preparation took place in analogy with Example 21c), starting with 4.19 g of 1-(4-methoxyphenyl)butane-1,2,3-trione 2-oxime (48). The following was obtained: 49. $C_{11}H_{11}N_3O_2$ (217.23) MS (ESI) 218 (M+H)

d) 5-(4-Methoxyphenyl)-3-methyl-1H-pyrazol-4-ylamine (50)

The preparation took place in analogy with Example 21d), starting with 3.17 g of 5-(4-methoxyphenyl)-3-methyl-4-nitro-1H-pyrazole (49). The following was obtained: 50. $C_{11}H_{13}N_3O$ (203.25) MS (ESI) 204 (M+H)

e) N-[5-(4-Methoxyphenyl)-3-methyl-1H-pyrazol-4-yl]benzamide (51)

The preparation took place in analogy with Example 15a), starting with 500 mg of 5-(4-methoxyphenyl)-3-methyl-1H-pyrazol-4-ylamine (50) and 315 μl of benzoyl chloride. The following was obtained: 51

$C_{18}H_{17}N_3O_2$ (307.36) MS (ESI) 308 (M+H)

f) 7-Methoxy-3-methyl-5-phenyl-1H-pyrazolo[4,3-c]isoquinoline (46)

The preparation took place in analogy with Example 1b), starting with 230 mg of N-[5-(4-methoxyphenyl)-3-methyl-1H-pyrazol-4-yl]benzamide (51). The following was obtained: 46

$C_{18}H_{15}N_3O$ (289.34) MS (ESI) 290 (M+H)

Example 22A

7-Methoxy-3-methyl-5-phenyl-1H-pyrazolo[4,3-c]isoquinoline (46)

The title compound was also prepared by a modified procedure as described herein using the procedures as set forth below.

a) 5-(4-Methoxy-phenyl)-3-methyl-1H-pyrazol-4-ylamine (A2) (Example 22(d)

6.80 g of sodium dithionite was added to a mixture of 1.23 g of 5-(4-methoxy-phenyl)-3-methyl-4-nitroso-1H-pyrazole (Example 22(c)) and 50 ml of water at 70° C., and the reaction mixture was stirred for 15 minutes. 5 ml of ethanol was added and the reaction mixture was stirred for 10 minutes. The reaction mixture was extracted with ethyl acetate. The organic layer was washed with brine, dried over magnesium sulfate, filtered and concentrated. Trituration with ether gave the title compound as a beige solid, melting point 120–122° C., $C_{11}H_{13}N_3O$ (203.24), MS (ESI, method B) 204 (M+H).

b) N-[5-(4-Methoxy-phenyl)-3-methyl-1H-pyrazol-4-yl]-benzamide (A1)

Example 22 (e)

110 μL of pyridine were added to a solution of 230 mg of 5-(4-methoxy-phenyl)-3-methyl-1H-pyrazol-4-ylamine in 10 ml of dichloromethane, followed immediately by 174 mg of benzoyl chloride. The reaction mixture was stirred at room temperature for 2 h and then concentrated. The residue was purified by MPLC, eluting with 80/20 ethyl acetate/heptane to give the title compound as a white solid, melting point 230–232° C., $C_{18}H_{17}N_3O_2$ (307.36), MS (ESI, method B) 308 (M+H).

c) 7-Methoxy-3-methyl-5-phenyl-1H-pyrazolo[4,3-c]isoquinoline (A)

Example 22(f)

740 mg of phosphorus pentoxide were added to a solution of 108 mg of N-[5-(4-Methoxy-phenyl)-3-methyl-1H-pyrazol-4-yl]-benzamide in 1.7 mL of phosphorus oxychloride and the reaction solution was stirred at reflux for 4.5 h. After cooling, ice was added carefully, followed by a saturated solution of sodium hydrogen carbonate. The whole was extracted with ethyl acetate. The organic phase was washed with brine, dried over sodium sulfate, concentrated under reduced pressure and the residue was purified by means of MPLC, eluting with 50/50 heptane/ethyl acetate. This gave the title compound as an off-white solid, $C_{18}H_{15}N_3O$ (289.34), MS (ESI, method A) 290 (M+H), HPLC $R_T$ 2.87 min.

Example 23

7,8-Dimethoxy-5-(3-methoxyphenyl)-3-methyl-1H-pyrazolo-[4,3-c]isoquinoline (52)

a) N-[5-(3,4-Dimethoxyphenyl)-3-methyl-1H-pyrazol-4-yl]-3-methoxybenzamide (53)

The preparation took place in analogy with Example 15a), starting with 300 mg of 5-(3,4-dimethoxyphenyl)-3-methyl-1H-pyrazol-4-ylamine (44) and 242 mg of 3-methoxybenzoyl chloride. The following was obtained: 53

$C_{20}H_{21}N_3O_4$ (367.41) MS (ESI) 368 (M+H)

b) 7,8-Dimethoxy-5-(3-methoxyphenyl)-3-methyl-1H-pyrazolo[4,3-c]isoquinoline (52)

The preparation took place in analogy with Example 1b), starting with 291 mg of N-[5-(3,4-dimethoxyphenyl)-3-methyl-1H-pyrazol-4-yl]-3-methoxybenzamide (53). The following was obtained: 52

$C_{20}H_{19}N_3O_3$ (349.39) MS (ESI) 350 (M+H)

Example 24

7,8-Dimethoxy-3-methyl-5-pyridin-2-yl-1H-pyrazolo[4,3-c]isoquinoline (54)

a) N-[5-(3,4-Dimethoxyphenyl)-3-methyl-1H-pyrazol-4-yl]pyridine-2-carboxamide (55)

The preparation took place in analogy with Example 15a), starting with 200 mg of 5-(3,4-dimethoxyphenyl)-3-methyl-1H-pyrazol-4-ylamine (44) and 168 mg of pyridine-2-carbonyl chloride*HCl. The following was obtained: 55

$C_{18}H_{18}N_4O_3$ (338.37); MS (ESI) 339 (M+H)

b) 7,8-Dimethoxy-3-methyl-5-pyridin-2-yl-1H-pyrazolo-[4,3-c]isoquinoline (54)

The preparation took place in analogy with Example 1b), starting with 160 mg of N-[5-(3,4-dimethoxyphenyl)-3-methyl-1H-pyrazol-4-yl]pyridine-2-carboxamide (55). The following was obtained: 54

$C_{20}H_{19}N_3O_3$ (320.35) MS (ESI) 321 (M+H)

Example 25

7,8-Dimethoxy-3-methyl-5-pyridin-3-yl-1H-pyrazolo[4,3-c]isoquinoline (56)

a) N-[5-(3,4-Dimethoxyphenyl)-3-methyl-1H-pyrazol-4-yl]nicotinamide (57)

The preparation took place in analogy with Example 15a), starting with 200 mg of 5-(3,4-dimethoxyphenyl)-3-methyl-1H-pyrazol-4-ylamine (44) and 168 mg of nicotinoyl chloride*HCl. The following was obtained: 57.

$C_{18}H_{18}N_4O_3$ (338.37) MS (ESI) 339 (M+H)

b) 7,8-Dimethoxy-3-methyl-5-pyridin-3-yl-1H-pyrazolo[4,3-c]isoquinoline (56)

The preparation took place in analogy with Example 1b), starting with 126 mg of N-[5-(3,4-dimethoxyphenyl)-3-methyl-1H-pyrazol-4-yl]nicotinamide (57). The following was obtained: 56

$C_{20}H_{19}N_3O_3$ (320.35) MS (ESI) 321 (M+H)

Example 26

7-Methoxy-5-(3-methoxyphenyl)-3-methyl-1H-pyrazolo-[4,3-c]isoquinoline (58)

a) 3-Methoxy-N-[5-(4-methoxyphenyl)-3-methyl-1H-pyrazol-4-yl]benzamide (59)

The preparation took place in analogy with Example 15a), starting with 300 mg of 5-(4-methoxyphenyl)-3-methyl-1H-pyrazol-4-ylamine (50) and 277 mg of 3-methoxybenzoyl chloride. The following was obtained: 59.

$C_{19}H_{19}N_3O_3$ (337.38) MS (ESI) 338 (M+H)

b) 7-Methoxy-5-(3-methoxyphenyl)-3-methyl-1H-pyrazolo[4,3-c]isoquinoline (58)

The preparation took place in analogy with Example 1b), starting with 263 mg of 3-methoxy-N-[5-(4-methoxyphenyl)-3-methyl-1H-pyrazol-4-yl]benzamide (59). The following was obtained: 58

$C_{19}H_{17}N_3O_2$ (319.37) MS (ESI) 320 (M+H)

Example 27

5-Phenyl-1H-pyrazolo[4,3-c]isoquinoline-3-carboxylic acid (60)

2.1 g of potassium permanganate in 36 ml of water were added to a solution of 600 mg of 5-phenyl-3-methyl-1H-pyrazolo[4,3-c]isoquinoline in 36 ml of pyridine. The mixture was stirred at 40° C. for 12 h. The resulting suspension was filtered with suction through silica gel, after which the filtrate was concentrated under reduced pressure and the residue was purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 60.

$C_{17}H_{11}N_3O_2$ (289.30) MS (ESI) 290 (M+H)

Example 28

Methyl 5-phenyl-1H-pyrazolo[4,3-c]isoquinoline-3-carboxylate (61)

18 μL of thionyl chloride were initially introduced into 0.5 ml of methanol and the mixture was stirred for 30 min. 19 mg of 5-phenyl-1H-pyrazolo[4,3-c]isoquinoline-3-carboxylic acid (60) in 0.5 ml of methanol were then added dropwise. The mixture was stirred at RT for 12 h, after which a saturated solution of sodium hydrogen carbonate was added and the whole was extracted, in each case 1×, with ethyl acetate and methylene chloride. The organic phases were combined, dried over magnesium sulfate and concentrated under reduced pressure and the residue was purified by means of HPLC (Merk-Hibar-Lichrospher 100-RP-18, water (0.1% trifluoroacetic acid)/acetonitrile (0.1% trifluoroacetic acid)=80/20→10/90). The following was obtained: 61.

$C_{18}H_{13}N_3O_2$ (303.32) MS (ESI) 304 (M+H)

Example 29

(5-Phenyl-1H-pyrazolo[4,3-c]isoquinolin-3-yl)methanol (62)

7.5 mg of lithium aluminum hydride were initially introduced into 1.5 ml of tetrahydrofuran and the mixture was stirred for 10 min. 6 mg of methyl 5-phenyl-1H-pyrazolo[4,3-c]isoquinoline-3-carboxylate (61) in 1.5 ml of tetrahydrofuran were then added dropwise. The mixture was stirred at 80° C. for 3 h, after which water was added and the whole was extracted with methylene chloride. The organic phase was dried over magnesium sulfate and concentrated under reduced pressure, and the residue was purified by means of HPLC (Merk-Hibar-Lichrospher 100-RP-18, water (0.1% trifluoroacetic acid)/acetonitrile (0.1% trifluoroacetic acid) 80/20→10/90). The following was obtained: 62.

$C_{17}H_{13}N_3O_1$ (275.31) MS (ESI) 276 (M+H)

Example 30

2-(3-Methyl-1H-pyrazolo[4,3-c]isoquinolin-5-yl)phenol (63)

The preparation takes place in analogy with Example 3, using 210 mg of 5-(2-methoxyphenyl)-3-methyl-1H-pyrazolo[4,3-c]isoquinoline (6). The following was obtained: 63.

$C_{17}H_{13}N_3O$ (275.31) MS (ESI) 276 (M+H)

Example 31

4-(3-Methyl-1H-pyrazolo[4,3-c]isoquinolin-5-yl)benzene-2,4-diol (64)

The preparation took place in analogy with Example 3, starting with 9 mg of 5-(3,5-dimethoxyphenyl)-3-methyl-1H-pyrazolo[4,3-c]isoquinoline (16). The following was obtained: 64. $C_{17}H_{13}N_3O_2$ (291.31); MS (ESI) 292 (M+H)

Example 32

4-(3-Methyl-1H-pyrazolo[4,3-c]isoquinolin-5-yl)benzene-1,2-diol (65)

The preparation took place in analogy with Example 3, starting with 40 mg of 5-(2,3-dimethoxyphenyl)-3-methyl- 1H-pyrazolo[4,3-c]isoquinoline (8). The following was obtained: 65.

$C_{17}H_{13}N_3O_2$ (291.31); MS (ESI) 292 (M+H)

Example 33

3-Methyl-5-phenyl-1H-pyrazolo[4,3-c]isoquinoline (B)

a) N-(3-Methyl-5-phenyl-1H-pyrazol-4-yl)-benzamide (B1).

To a rt solution of 550 mg of 3-methyl-5-phenyl-1H-pyrazol-4-ylamine (prepared in accordance with the procedure set forth in UK 2 185 255, Example 2A) in 8.5 mL pyridine was added 370 µL of benzoyl chloride. The reaction was stirred for 1 h and then concentrated under reduced pressure. The residue was dissolved in chloroform and washed with 0.5 N hydrochloric acid and then saturated aqueous sodium carbonate. The organic portion was dried with sodium sulfate and concentrated under reduced pressure and purified by means of MPLC (12 g $SiO_2$, 40% ethyl acetate:heptane) to give the title compound as a colorless solid.

HPLC $R_T$=2.35 min.

$C_{17}H_{15}N_3O$ (277.33) MS, (ESI, method A) 278 (M+H).

b) 3-Methyl-5-phenyl-1H-pyrazolo[4,3-c]isoquinoline (B).

To a mixture of 565 mg of N-(3-Methyl-5-phenyl-1H-pyrazol-4-yl)-benzamide was added 5 mL of nitrobenzene followed by 270 µL of $POCl_3$ and the resulting mixture was heated at 185° C. After 1 h, 0.4 mL of a $SnCl_4$ solution (1.0 M solution in heptane) was added and the mixture was heated for an additional 2 h, then concentrated under reduced pressure and purified by means of MPLC (12 g $SiO_2$, 35% ethyl acetate:heptane) to give the title compound as a tan solid.

HPLC $R_T$=2.85 min.

$C_{17}H_{13}N_3$ (259.31) MS, (ESI, method A) 260 (M+H).

Example 34

3-Methyl-5-thiophen-2-yl-1H-pyrazolo[4,3-c]isoquinoline (D)

a) Thiophene-2-carboxylic acid (3-methyl-5-phenyl-1H-pyrazol-4-yl)-amide (D1).

The preparation took place in analogy to Example 33(B1) starting with 120 µL of 2-thiophenecarbonyl chloride, except the product was purified using MPLC (12 g $SiO_2$, 30% ethyl acetate:heptane) to give the title compound as an amorphous, orange solid.

HPLC $R_T$=2.28 min.

$C_{15}H_{13}N_3OS$ (283.36) MS (ESI, method A) 284 (M+H).

b) 3-Methyl-5-thiophen-2-yl-1H-pyrazolo[4,3-c]isoquinoline (D).

To a suspension of 682.4 mg of thiophene-2-carboxylic acid (3-methyl-5-phenyl-1H-pyrazol-4-yl)-amide in 11.0 mL of phosphorous oxychloride was added 5.00 g of phosphorous pentoxide and the resulting suspension was heated at 120° C. for 5 h. The reaction mixture was cooled to rt and quenched with the addition of ice and water and then neutralized with solid sodium carbonate. The aqueous mixture was extracted with ethyl acetate and the combined organic extracts were washed with brine, dried (magnesium sulfate) and concentrated under reduced pressure. The residue was purified by means of MPLC (4 g $SiO_2$, 30% ethyl acetate:dichloromethane) to give the title compound as a tan solid.

HPLC $R_T$=3.19 min.

$C_{15}H_{11}N_3S$ (265.34) MS (ESI, method A) 266 (M+H).

Example 35

5-Furan-2-yl-3-methyl-1H-pyrazolo[4,3-c]isoquinoline a) Furan-2-carboxylic acid (3-methyl-5-phenyl-1H-pyrazol-4-yl)-amide (E1).

To a RT solution of 337.3 mg of 3-methyl-5-phenyl-1H-pyrazol-4-ylamine in 4 mL methylene chloride was added 407 µL of triethylamine and 201 µL of 2-furoyl chloride. After 2 h at RT, the reaction mixture was concentrated under reduced pressure and the residue was dissolved in chloroform and washed with saturated aqueous sodium carbonate and brine. The organic portion was dried with sodium sulfate and concentrated under reduced pressure. The residue contained the title compound as a yellow, amorphous solid and was used without further purification.

HPLC $R_T$=2.08 min.

$C_{15}H_{13}N_3O_2$ (267.30) MS (ESI, method A) 268 (M+H).

b) 5-Furan-2-yl-3-methyl-1H-pyrazolo[4,3-c]isoquinoline (E).

The preparation took place in analogy to Example 33 (B) starting with 419.1 mg of the product from Example 35a (E1), except the residue was purified by means of MPLC (12 g $SiO_2$, 20% ethyl acetate:dichloromethane) to give the title compound as a light yellow solid.

HPLC $R_T$=2.73 min.

$C_{15}H_{11}N_3O$ (249.29) MS (ESI, method A) 250 (M+H).

Example 36

5-(3-Chloro-benzo[b]thiophen-2-yl)-3-methyl-1H-pyrazolo[4,3-c]isoquinoline.

a) 3-Chloro-benzo[b]thiophene-2-carboxylic acid (3-methyl-5-phenyl-1H-pyrazol-4-yl)-amide (F1).

The preparation took place in analogy to Example 35 (E1) starting with 627 mg of 3-chlorobenzo[b]thiophene-2-carbonyl chloride. The title compound was obtained as an off-white solid.

HPLC $R_T$=3.08 min.

$C_{19}H_{14}ClN_3OS$ (367.86) MS (ESI, method A) 368 (M+H).

b) 5-(3-Chloro-benzo[b]thiophen-2-yl)-3-methyl-1H-pyrazolo[4,3-c]isoquinoline (F).

The preparation took place in analogy to Example 34 (D) starting with 484 mg of 3-chloro-benzo[b]thiophene-2-carboxylic acid (3-methyl-5-phenyl-1H-pyrazol-4-yl)-amide. The title compound was obtained as a light tan solid.

HPLC $R_T$=3.63 min.

$C_{19}H_{12}ClN_3S$ (349.85) MS (ESI, method A) 350 (M+H).

Example 37

5-(6-Chloro-pyridin-3-yl)-3-methyl-1H-pyrazolo[4,3-c]isoquinoline a) 6-Chloro-N-(3-methyl-5-phenyl-1H-pyrazol-4-yl)-nicotinamide (G1).

The preparation took place in analogy to Example 35 (E1) starting with 426 mg of 6-chloronicotinoyl chloride. The title compound was obtained as a colorless solid.

HPLC $R_T$=2.27 min.
$C_{16}H_{13}ClN_4O$ (312.76) MS (ESI, method A) 313 (M+H).

b) 5-(6-Chloro-pyridin-3-yl)-3-methyl-1H-pyrazolo[4,3-c]isoquinoline (G).

The preparation took place in analogy to Example 34 (D) starting with 400 mg of 6-chloro-N-(3-methyl-5-phenyl-1H-pyrazol-4-yl)-nicotinamide, except the reaction time was 48 h. The title compound was obtained as a light tan solid.

HPLC $R_T$=2.70 min.
$C_{16}H_{11}ClN_4$ (294.07) MS (ESI, method A) 295 (M+H).

Example 38

5-(2-Chloro-pyridin-3-yl)-3-methyl-1H-pyrazolo[4,3-c]isoquinoline a) 2-Chloro-N-(3-methyl-5-phenyl-1H-pyrazol-4-yl)-nicotinamide (H1).

The preparation took place in analogy to Example 35 (E1) starting with 404 mg of 2-chloronicotinoyl chloride. The title compound was obtained as a tan, amorphous solid.

HPLC $R_T$=2.03 min.
$C_{16}H_{13}ClN_4O$ (312.76) MS (ESI, method A) 313 (M+H).

b) 5-(2-Chloro-pyridin-3-yl)-3-methyl-1H-pyrazolo[4,3-c]isoquinoline (H).

The preparation took place in analogy to Example 34 (D) starting with 511.5 mg of 2-chloro-N-(3-methyl-5-phenyl-1H-pyrazol-4-yl)-nicotinamide, except the reaction time was 36 h, and the residue was purified by means of MPLC (4 g $SiO_2$, 40% ethyl acetate:dichloromethane) to give the title compound as a light tan solid.

HPLC $R_T$=2.42 min.
$C_{16}H_{11}ClN_4$ (294.76) MS, method A (ESI) 295 (M+H).

Example 39

5-Benzo[b]thiophene-2-yl-3-methyl-1H-pyrazolo[4,3-c]isoquinoline a) 5-Benzo[b]thiophene-2-carboxylic acid (3-methyl-5-phenyl-1H-pyrazol-4-yl)-amide (I1).

The preparation took place in analogy to Example 33 (B1) starting with 380 mg of 3-methyl-5-phenyl-1H-pyrazol-4-ylamine in 4.6 mL pyridine and 454 mg benzo[b]thiophene-2-carbonyl chloride. The residue after work-up contained the title compound as a yellow solid and was used without further purification.

HPLC $R_T$=2.77 min.
$C_{19}H_{15}N_3OS$ (333.41) MS (ESI, method A) 334(M+H).

b) 5-Benzo[b]thiophene-2-yl-3-methyl-1H-pyrazolo[4,3-c]isoquinoline (I).

The preparation took place in analogy to Example 34 (D) starting with 544 mg of benzo[b]thiophene-2-carboxylic acid (3-methyl-5-phenyl-1H-pyrazol-4-yl)-amide, except the residue was purified by being recrystallisation from ethyl acetate to give the title compound as a tan solid.

HPLC $R_T$=3.62 min.
$C_{19}H_{13}N_3S$ (315.40) MS (ESI, method A) 316 (M+H).

Example 40

3-Methyl-5-(3-methyl-benzofuran-2-yl)-1H-pyrazolo[4,3-c]isoquinoline.

a) 3-Methyl-benzofuran-2-carboxylic acid (3-methyl-5-phenyl-1H-pyrazol-4-yl)-amide (J1).

The preparation took place in analogy to Example 39 (I1) starting with 492 mg of 3-methylbenzofuran-2-carbonyl chloride. The title compound was obtained as a yellow, amorphous solid.

HPLC $R_T$=2.88 min.
$C_{20}H_{17}N_3O_2$ (331.38) MS (ESI, method A) 332 (M+H).

b) 3-Methyl-5-(3-methyl-benzofuran-2-yl)-1H-pyrazolo[4,3-c]isoquinoline (J).

The preparation took place in analogy to Example 39 (I) starting with 735 mg of 3-methyl-benzofuran-2-carboxylic acid (3-methyl-5-phenyl-1H-pyrazol-4-yl)-amide. The title compound was obtained as a brown solid.

HPLC $R_T$=3.58 min.
$C_{20}H_{15}N_3O$ (313.37) MS (ESI, method A) 314 (M+H).

Example 41

3-Methyl-5-quinoxalin-2-yl-1H-pyrazolo[4,3-c]isoquinoline a) Quinoxaline-2-carboxylic acid (3-methyl-5-phenyl-1H-pyrazol-4-yl)-amide (K1)

The preparation took place in analogy to Example 38 (H1) starting with 393.4 mg of 2-quinoxaloyl chloride. The title compound was obtained as a maroon solid.

HPLC $R_T$=2.57 min.
$C_{19}H_{15}N_5O$ (329.36) MS (ESI, method A) 330 (M+H).

b) 3-Methyl-5-quinoxalin-2-yl-1H-pyrazolo[4,3-c]isoquinoline (K)

The preparation took place in analogy to Example 34 (D) starting with 423 mg of quinoxaline-2-carboxylic acid (3-methyl-5-phenyl-1H-pyrazol-4-yl)-amide, except the residue was purified by recrystallisation from methanol. The title compound was obtained as a tan solid.

HPLC $R_T$=3.34 min
$C_{19}H_{13}N_5$ (311.35) MS (ESI, method A) 312 (M+H).

Example 42

5-Isoxazol-5-yl-3-methyl-1H-pyrazolo[4,3-c]isoquinoline a) Isoxazole-5-carboxylic acid (3-methyl-5-phenyl-1H-pyrazol-4-yl)-amide (L1).

The preparation took place in analogy to Example 39 (I1) starting with 315 mg of isoxazole-5-carbonyl chloride. The title compound was obtained as a tan solid.

HPLC $R_T$=1.97 min.
$C_{14}H_{12}N_4O_2$ (268.28) MS (ESI, method A) 269 (M+H).

b) 5-Isoxazol-5-yl-3-methyl-1H-pyrazolo[4,3-c]isoquinoline (L).

The preparation took place in analogy to Example 34 (D) starting with 274.6 mg of isoxazole-5-carboxylic acid (3-methyl-5-phenyl-1H-pyrazol-4-yl)-amide, except the reaction time was 24 h and the residue was purified by means of MPLC (4 g $SiO_2$, 40% ethyl acetate:dichloromethane) to give the title compound as an off-white solid.

HPLC $R_T$=2.45 min.

$C_{14}H_{10}N_4O$ (250.26) MS (ESI, method A) 251 (M+H).

Example 43

3-Methyl-5-(1-methyl-1H-pyrrol-2-yl)-1H-pyrazolo[4,3-c]isoquinoline a) 1-Methyl-1H-pyrrole-2-carboxylic acid (3-methyl-5-phenyl-1H-pyrazol-4-yl)-amide (M1).

The preparation took place in analogy to Example 39 (I1) starting with 301 mg of N-methylpyrrole-2-carbonyl chloride. The title compound was obtained as a tan, amorphous solid.

HPLC $R_T$=2.33 min.

$C_{16}H_{16}N_4O$ (280.34) MS (ESI, method A) 281 (M+H).

b) 3-Methyl-5-(1-methyl-1H-pyrrol-2-yl)-1H-pyrazolo[4,3-c]isoquinoline (M).

The preparation took place in analogy to Example 34 (D) starting with 432 mg of 1-methyl-1H-pyrrole-2-carboxylic acid (3-methyl-5-phenyl-1H-pyrazol-4-yl)-amide, except the residue was purified by means of MPLC (4 g $SiO_2$, 40% ethyl acetate:dichloromethane) to give the title compound as a yellow solid.

HPLC $R_T$=2.72 min.

$C_{16}H_{14}N_4$ (262.32) MS (ESI, method A) 263 (M+H).

Example 44

3-Methyl-5-(3-methyl-thiophen-2-yl)-1H-pyrazolo[4,3-c]isoquinoline a) 3-Methyl-thiophene-2-carboxylic acid (3-methyl-5-phenyl-1H-pyrazol-4-yl)-amide (N1).

The preparation took place in analogy to Example 39 (I1) starting with 414 mg of 3-methylthiophene-2-carbonyl chloride. The title compound was obtained as a tan solid.

HPLC $R_T$=2.45 min.

$C_{15}H_{16}N_3OS$ (297.39) MS (ESI, method A) 298 (M+H).

b) 3-Methyl-5-(3-methyl-thiophen-2-yl)-1H-pyrazolo[4,3-c]isoquinoline (N).

The preparation took place in analogy to Example 34 (D) starting with 562 mg of 3-methyl-thiophene-2-carboxylic acid (3-methyl-5-phenyl-H-pyrazol-4-yl)-amide, except the residue was dissolved in methanol and then purified by MPLC (4 g $SiO_2$, 10% ethyl acetate:dichloromethane, more polar fraction) to yield the title compound as a tan solid, along with the N-methylated compound (see, Example 45 (O) below).

HPLC $R_T$=2.95 min.

$C_{16}H_{13}N_3S$ (279.08) MS (ESI, method A) 280 (M+H).

Example 45

1,3-Dimethyl-5-(3-methyl-thiophen-2-yl)-1H-pyrazolo[4,3-c]isoquinoline a) 1,3-Dimethyl-5-(3-methyl-thiophen-2-yl)-1H-pyrazolo[4,3-c]isoquinoline (O).

The compound was isolated along with 3-methyl-5-(3-methyl-thiophen-2-yl)-1H-pyrazolo[4,3-c]isoquinoline (compound N of Example 44 above) by means of MPLC (4 g $SiO_2$, 10% ethyl acetate:dichloromethane, less polar fraction) to yield the title compound as a tan solid.

HPLC $R_T$=3.25 min.

$C_{17}H_{15}N_3S$ (293.10) MS (ESI, method A) 294 (M+H).

Example 46

5-phenyl-3-ethyl-1H-pyrazolo[4,3-c]isoquinoline a) 1-Phenylpentan-1,3-dione-2-oxime (P4)

This compound was prepared in accordance with the procedures set forth in Saloutin et al, J. Flourine Chem, vol 84, pp 107–111 as described herein. A stirred suspension of 8.8 g of 1-phenylpentan-1,3-dione in 25 mL of glacial acetic acid was treated with a solution of 3.85 g of sodium nitrite in 20 mL of water maintaining the temperature below 15° C. The reaction mixture was allowed to warm to rt and stirred for 4 h. The reaction mixture was diluted with 100 mL of water and extracted with ethyl acetate. The organic portion was washed with water and brine and dried over magnesium sulfate. Concentration gave the title compound as a yellow solid, melting point 87–88° C.

$C_{11}H_{11}NO_3$ (205.23), MS (ESI, method B) 204 (M–H).

TLC (3/7 ethyl acetate/heptane) $R_f$=0.3.

b) 3-Ethyl-4-nitroso-5-phenyl-1H-pyrazole (P3)

A solution of 9.45 g of 1-phenylpentan-1,3-dione-2-oxime in 100 mL of ethanol was cooled to 0° C. and treated with a solution of 2.7 mL of hydrazine hydrate in 10 mL of ethanol and stirred at RT overnight. The reaction mixture was evaporated to dryness and the residue dissolved in ethyl acetate. The organic portion was washed with water and brine and dried over magnesium sulfate. Concentration gave a green oil that solidified on standing, which was purified by MPLC, eluting with 3/2 ethyl acetate/heptane, to give the title compound as a brown semi-solid.

$C_{11}H_{11}N_3O$ (201.23), MS (ESI, method B) 200 (M–H)

TLC (1/1 ethyl acetate/heptane) $R_f$=0.25.

c) 4-Amino-3-ethyl-5-phenyl-1H-pyrazole (P2)

A solution of 6.3 g of 3-ethyl-4-nitroso-5-phenyl-1H-pyrazole in 220 mL of ethanol was treated with 2.0 g of 10% palladium/carbon catalyst and hydrogenated at RT and 50 psi for 16 h. The reaction mixture was filtered through celite and washed well with ethanol. The filtrate was concentrated to give the title compound as a brown oil.

$C_{11}H_{13}N_3$ (187.25), MS (ESI, method B) 188 (M+H).

TLC (1/1 ethyl acetate/heptane) $R_f$=0.28.

d) N-(3-Ethyl-5-phenyl-1H-pyrazol-4-yl)-benzamide (P1)

The preparation took place in analogy to Example A1 using 2.0 mL of benzoyl chloride, except the reaction mixture was stirred at RT for 5 hours and then concentrated. The residue was partitioned between ethyl acetate and water. The organic portion was washed with brine and dried over magnesium sulphate. Concentration and purification by HPLC, eluting with 2/3 ethyl acetate/heptane, gave the title compound as a white solid, melting point 215–216° C.

$C_{18}H_{17}N_3O$ (291.14), MS (ESI, method B) 292 (M+H)
HPLC $R_T$ 2.47 min e) 5-Phenyl-3-ethyl-1H-pyrazolo[4,3-c]isoquinoline (P)

The preparation took place in analogy to Example 34 (D) using 0.87 g of N-(3-ethyl-5-phenyl-1H-pyrazol-4-yl)-benzamide, except the residue was recrystallised from methanol to give the title compound as a tan crystalline solid, melting point 250–251° C.

$C_{18}H_{15}N_3$ (273.13), MS (ESI, method B) 272 (M–H).
HPLC $R_T$=3.03 min

Example 47

3-Ethyl-5-(pyridin-3-yl)-1H-pyrazolo[4,3-c)isoquinoline a) N-(Pyridin-3-yl)-(3-ethyl-5-phenyl-1H-pyrazol-4-yl) amide (Q1)

The preparation took place in analogy to Example 22e using 420 mg of nicotinoyl chloride hydrochloride and 0.383 ml of pyridine, stirring at RT for 16 h. The reaction mixture was washed with water and brine, and the organic portion was dried over magnesium sulfate then concentrated. The residue was purified by MPLC, eluting with 3/1 ethyl acetate/heptane to give the title compound as a white solid, melting point 212–213° C.

$C_{17}H_{16}N_4O$ (292.35), MS (ESI, method A) 293 (M+H)
HPLC $R_T$=1.85 min b) 3-Ethyl-5-(pyridin-3-yl)-1H-pyrazolo[4,3-c)isoquinoline (Q)

The preparation took place in analogy to Example 34 (D) using 700 mg of N-(pyridin-3-yl)-(3-ethyl-5-phenyl-1H-pyrazol-4-yl)amide, refluxing for 6 h. The residue was purified by MPLC, eluting with 4/1 ethyl acetate/heptane, to give the title compound as a white solid, melting point 219–220° C.

$C_{17}H_{14}N_4$ (274.23), MS (ESI, method A) 275 (M+H)
HPLC $R_T$=2.29 min

Example 48

5-(2,6-difluoro-phenyl)-3-methyl-1H-pyrazole[4,3-c] isoquinoline, trifluoroacetic acid salt a) 2,6-Difluoro-N-(3-methyl-5-phenyl H-pyrazol-4-yl)-benzamide (R1)

268.5 mg of 2,6-difluorobenzoyl chloride was added dropwise to a solution of 263.4 mg of 3-methyl-5-phenyl-1H-pyrazol-4-ylamine in 4.5 ml of pyridine at room temperature. The reaction mixture was stirred for 24 h, the precipitate formed was filtered off and washed with dichloromethane to give the title compound.

HPLC $R_T$=2.37 min
$C_{17}H_{13}F_2N_3O$ (313.31) MS (ESI, method A) 314 (M+H)

b) 5-(2,6-Difluoro-phenyl)-3-methyl-1H-pyrazole[4,3-c] isoquinoline, trifluoroacetic acid salt (R)

The preparation took place in analogy to example 33 (B), starting with 188 mg of 2,6-difluoro-N-(3-methyl-5-phenyl H-pyrazol-4-yl)-benzamide, except the residue was purified by MPLC (4 g $SiO_2$, dichloromethane/methanol, gradient of 95/5→40/60). Further purification by preparative HPLC (Monochrome 10u C18 100×21.2 mm column, water (0.1% trifluoroacetic acid)/acetonitrile (0.1% trifluoroacetic acid), gradient of 95/5→0/100) gave the title compound.

HPLC $R_T$ 2.77 min
$C_{17}H_{11}F_2N_3$ (295.09), MS (ESI, method A) 296 (M+H)

Example 49

5-(2-Chloro-phenyl)-3-methyl-1H-pyrazolo[4,3-c] isoquinoline a) 2-Chloro-N-(3-methyl-5-phenyl-1H-pyrazol-4-yl)-benzamide (S1)

The preparation took place in analogy to Example 33 (B1), starting with 266 mg of 2-chloro-benzoylchloride, except the reaction mixture was stirred for 24 h before concentrating. Trituration of the residue with dichloromethane gave the title compound as a white precipitate.

HPLC $R_T$ 2.42 minutes
$C_{17}H_{14}ClN_3O$ (312.06) MS (ESI, method A) 313 (M+H)

b) 5-(2-chloro-phenyl)-3-methyl-1H-pyrazolo[4,3-c]isoquinoline (S)

The preparation took place in analogy to Example 33 (B), using 401 mg of 2-chloro-N-(3-methyl-5-phenyl-1H-pyrazol-4-yl)-benzamide. The reaction mixture was diluted with water and extracted with dichloromethane. The organic portion was concentrated under reduced pressure and purified by MPLC (4 g $SiO_2$, dichloromethane/methanol=99/1→50/50) to give the title compound.

HPLC $R_T$ 2.94 min
$C_{17}H_{12}ClN_3$ (293.76) MS (ESI, method A) 294 (M+H)

Example 50

5-(4-Fluoro-phenyl)-3-methyl-1H-pyrazolo[4,3-c] isoquinoline a) 4-Fluoro-N-(3-methyl-5-phenyl-1H-pyrazol-4-yl)-benzamide (T1)

The preparation took place in analogy to Example 48 (S1), starting with 241 mg of 4-fluorobenzoyl chloride to give the title compound as a white precipitate.

HPLC $R_T$ 2.46 minutes.
$C_{17}H_{14}FNO_3$ (295.31) MS (ESI, method A) 296 (M+H)

b) 5-(4-Fluoro-phenyl)-3-methyl-1H-pyrazolo[4,3-c]isoquinoline (T)

The preparation was carried out as in Example 22A using 236 mg of 4-fluoro-N-(3-methyl-5-phenyl-1H-pyrazol-4-yl)-benzamide, except the reaction mixture was refluxed for 10 h. The cream solid residue after workup was the title compound.

HPLC (Method A) $R_T$=3.20 min
$C_{17}H_{12}FN_3$ (297.30) MS (ESI) 278 M+H)

Example 51

3-Methyl-5-p-tolyl-1H-pyrazolo[4,3-c]isoquinoline a) 4-Methyl-N-(3-methyl-5-phenyl-1H-pyrazol-4-yl)-benzamide (U1)

The preparation took place in analogy to example 33 (B1), using 227 mg of p-toluoyl chloride. Concentration of the reaction mixture gave a solid that was triturated in dichloromethane to give the title compound.
HPLC R+2.55 min
$C_{18}H_{17}N_3O$ (291.36) MS (ESI, method A) 292(M+H)

b) 3-Methyl-5-p-tolyl-1H-pyrazolo[4,3-c]isoquinoline (U)

The preparation took place in analogy to example 33 (B), using 192 mg of 4-methyl-N-(3-methyl-5-phenyl-1H-pyrazol-4-yl)-benzamide, except the reaction mixture was diluted with water and extracted with dichloromethane. The organic portion was concentrated under reduced pressure and purified by MPLC (4 g $SiO_2$, dichloromethane/methanol, gradient=99/1→50/50) to give the title compound.
HPLC $R_T$ 3.08 min.
$C_{18}H_{15}N_3$ (273.34) MS (ESI, method A) 274 (M+H)

Example 52

3-Methyl-5-o-tolyl-1H-pyrazolo[4,3-c]isoquinoline a) 2-Methyl-N-(3-methyl-5-phenyl-1H-pyrazol-4-yl)benzamide (V1)

The preparation took place in analogy to example 33 (B1), using 301 mg of o-toluoyl chloride. Concentration of the reaction mixture gave a solid that was triturated with dichloromethane and then recrystallised from ethyl acetate to give the title compound.
HPLC $R_T$ 2.46 min
$C_{18}H_{17}N_3O$ (291.36) MS (ESI, method A) 292(M+H)

b) 3-Methyl-5-o-tolyl-1H-pyrazolo[4,3-c]isoquinoline (V)

The preparation took place in analogy to example 22A, using 303 mg of 2-methyl-N-(3-methyl-5-phenyl-1H-pyrazol-4-yl), except the reaction was heated for 4 h, and the residue was triturated in methanol to give the title compound.
HPLC $R_T$ 2.90 min
$C_{18}H_{15}N_3$ (273.34) MS (ESI, method A) 274(M+H)

Example 53

5-(4-Chlorophenyl)-3-methyl-1H-pyrazolo[4,3-c]isoquinoline a) 4-Chloro-N-(3-methyl-5-phenyl-1H-pyrazol-4-yl)-benzamide (W1)

The preparation took place in analogy to example 33 (B1), using 283 mg of 4-chlorobenzoyl chloride. Concentration of the reaction mixture gave a solid that was triturated with dichloromethane to give the title compound.
HPLC $R_T$ 2.66 min
$C_{17}H_{14}ClN_3O$ (311.77), MS (ESI, method A) 312(M+H)

b) 5-(4-Chlorophenyl)-3-methyl-1H-pyrazolo[4,3-c]isoquinoline (W)

The preparation took place in analogy to example 33 (B), using 289 mg of 4-chloro-N-(3-methyl-5-phenyl-1H-pyrazol-4-yl)-benzamide. The reaction mixture was partitioned between water and dichloromethane. The organic portion was concentrated and triturated with hot ethyl acetate. The tan solid residue was purified by MPLC (5 g $SiO_2$, solvent gradient of dichloromethane/methanol→100/0→0/100), to give the title compound.
HPCL $R_T$ 3.29 min
$C_{17}H_{12}ClN_3$ (293.07), MS (ESI, method A) 294 (M+H)

Example 54

5-(2-Fluorophenyl)-3-methyl-1H-pyrazolo[4,3-c]isoquinoline a) 2-Fluoro-N-(3-methyl-5-phenyl-1H-pyrazol-4-yl)-benzamide (X1)

The preparation took place in analogy to example 33 (B1), using 249 mg of 4-fluorobenzoyl chloride. The residue from concentration was triturated with dichloromethane. The solid obtained was purified by MPLC (5 g SiO2, methanol/dichloromethane=0/100→10/100) to give the title compound.
HPLC $R_T$ 2.43 min
$C_{17}H_{14}FN_3O$ (295.32) MS (ESI, method A) 296 (M+H)

b) 5-(2-Fluorophenyl)-3-methyl-1H-pyrazolo[4,3-c]isoquinoline (X)

The preparation took place in analogy to example 34 (D) using 182 mg of 2-fluoro-N-(3-methyl-5-phenyl-1H-pyrazol-4-yl)-benzamide, except 10.7 ml of phosphorous oxychloride was used and the reaction was stirred for 4 hrs. Trituration of the residue with ethyl acetate/dichloromethane (1/1) gave the title compound as a cream solid.
HPLC $R_T$ 2.82 min
$C_{17}H_{12}FN_3$ (277.10) MS (ESI, method A) 278 (M+H)

Example 55

5-(2,4-Difluorophenyl)-3-methyl-1H-pyrazolo[4,3-c]isoquinoline a) 2,4-Difluoro-N-(3-methyl-5-phenyl-1H-pyrazol-4-yl)-benzamide (Y1)

The preparation took place in analogy to example 33 (B1) using 297 mg of 2,4-difluorobenzoyl chloride. The residue was triturated with dichloromethane to give the title compound.
HPLC $R_T$ 2.53 min
$C_{17}H_{13}F_2N_3O$ (313.31) MS (ESI, method A) 314 (M+H)

b) 5-(2,4-Difluorophenyl)-3-methyl-1H-pyrazolo[4,3-c]isoquinoline (Y)

The preparation took place in analogy to example 33 (B) using 233 mg of 2,4-difluoro-N-(3-methyl-5-phenyl-1H-pyrazol-4-yl)-benzamide, except the reaction mixture was heated for 4 h after addition of $SnCl_4$, and addition of water gave a tan precipitate. This material was triturated with hot methanol to give a solid that was further triturated with dichloromethane and methanol to give the title compound as a white solid.
HPLC $R_T$ 2.93 min
$C_{17}H_{11}F_2N_3$ (295.09) MS (ESI, method A) 296 (M+H)

Example 56

3-Methyl-5-(3-methyl-phenyl)-1H-pyrazolo[4,3-c]isoquinoline a) 3-Methyl-N-(3-methyl-5-phenyl-1H-pyrazol-4-yl)-benzamide (Z1)

The preparation took place in analogy to Example 33 (B1) using 268 mg of m-toluoyl chloride. A white precipitate formed in the reaction mixture, which was collected by filtration, washed with ethyl acetate, dried under vacuum and identified as the title compound.

HPLC R$_T$ 2.56 min

C$_{18}$H$_{17}$N$_3$O (291.36) MS (ESI, method A) 292(M+H)

b) 3-Methyl-5-(3-methyl-phenyl)-1H-pyrazolo[4,3-c]isoquinoline (Z)

The preparation took place in analogy to example 34 (D) using 404 mg of 3-methyl-N-(3-methyl-5-phenyl-1H-pyrazol-4-yl)-benzamide, except 10 ml of phosphorous oxychloride was used and the reaction was stirred for 4 hrs. Trituration of the residue with dichloromethane/methanol (95/5) gave the title compound as an off white solid.

HPLC R$_T$ 3.29 min

C$_{18}$H$_{15}$N$_3$ (273.13) MS (ESI, method A) 274 (M+H)

Example 57

5-(2-Bromo-phenyl)-3-methyl-1H-pyrazolo[4,3-c]isoquinoline a) 2-Bromo-N-(3-methyl-5-phenyl-1H-pyrazole-4-yl)-benzamide (AA1)

The preparation took place in analogy to example 33 (B1) using 380.5 mg of 2-bromobenzoyl chloride, except the reaction mixture was stirred for 16 h. Purification of the residue by trituration with 1% methanol in dichloromethane gave the title compound.

HPLC R$_T$ 2.48 min

C$_{17}$H$_{14}$BrN$_3$O (355) MS (ESI, method A) 356 (M+H)

b) 5-(2-Bromo-phenyl)-3-methyl-1H-pyrazolo[4,3-c]isoquinoline (AA)

The preparation took place in analogy to example 34 (D) using 196 mg of 2-bromo-N-(3-methyl-5-phenyl-1H-pyrazole-4-yl)-benzamide, except 6 ml of phosphorous oxychloride was used and the reaction was stirred for 4 hrs. The residue was triturated with dichloromethane to give the title compound as a white solid.

HPLC R$_T$ 3.17 min

C$_{17}$H$_{12}$BrN$_3$ (337.02) MS (ESI, Method A) 338 (M+H)

Example 58

5-(2,4-Dichloro-phenyl)-3-methyl-1H-pyrazoloisoquinoline a) 2,4-Dichloro-N-(3-methyl-5-phenyl-1H-pyrazol-4-yl)-benzamide (AB1)

The preparation took place in analogy to example 33 (B1) using 363 mg of 2,4 dichlorobenzoyl chloride, except the reaction mixture was stirred for 16 h. The residue was triturated with ethyl acetate/dichloromethane (4/6) to give the title compound as a cream solid.

HPLC R$_T$ 2.74 min

C$_{17}$H$_{15}$Cl$_2$N$_3$O (345.04) MS (ESI, method A) 346(M+H)

b) 5-(2,4-Dichloro-phenyl)-3-methyl-1H-pyrazolo[4,3-c]isoquinoline (AB)

The preparation took place in analogy to example 34 (D) using 115 mg of 2,4-dichloro-N-(3-methyl-5-phenyl-1H-pyrazol-4-yl)-benzamide. The cream solid residue was found to be the title compound.

HPLC R$_T$ 3.49 min

C$_{17}$H$_{11}$Cl$_2$N$_3$ (327.03) MS (ESI, Method A) 328 (M+H)

Example 59

3-Methyl-5-(2,3,4,5,6-pentafluoro-phenyl)-1H-pyrazolo[4,3-c]isoquinoline a) 2,3,4,5,6-Pentafluoro-N-(3-methyl-5-phenyl-1H-pyrazol-4-yl)-benzamide (AC1)

The preparation took place in analogy to example 33 (B1) using 400 mg of 2,3,4,5,6-pentafluoro-benzoyl chloride. The residue was triturated with methanol/dichloromethane (95/5) to give the title compound.

HPLC R$_T$ 2.72 min

C$_{17}$H$_{10}$F$_5$N$_3$O (367.28) MS (ESI, method A) 368(M+H)

b) 3-Methyl-5-(2,3,4,5,6-pentafluoro-phenyl)-1H-pyrazolo[4,3-c]isoquinoline (AC)

The preparation was carried out as in Example 50 (T) using 147 mg of 2,3,4,5,6-pentafluoro-N-(3-methyl-5-phenyl-1H-pyrazol-4-yl)-benzamide, to give the title compound as a pale cream solid.

HPLC (Method A) R$_T$ 3.15 min

C$_{17}$H$_8$F$_5$N$_3$ (349.06) MS (ESI, Method A) 350 (M+H)

Example 60

5-(3,4-Dichloro-phenyl)-3-methyl-1H-pyrazolo[4,3-c]isoquinoline a) 3,4-Dichloro-N-(3-methyl-5-phenyl-1H-pyrazol-4-yl)-benzamide (AD1)

The preparation was carried out as in Example 33 (B1) using 368 mg of benzoyl chloride, except the reaction mixture was stirred for 70 h. The cream solid from the work-up was found to be the title compound.

HPLC (Method A) R$_T$ 2.87 min

C$_{17}$H$_{13}$Cl$_2$N$_3$O 345.04 MS (ESI, Method A) 346.05 (M+H)

b) 5-(3,4-Dichloro-phenyl)-3-methyl-1H-pyrazolo[4,3-c]isoquinoline (AD)

The preparation was carried out as in Example 22A, using 484 mg of 3,4-dichloro-N-(3-methyl-5-phenyl-1H-pyrazol-4-yl)-benzamide. Work up gave the title compound as a beige solid, which did not need further purification.

HPLC (Method B) R$_T$ 3.61 min

C$_{17}$H$_{11}$Cl$_2$N$_3$ 327 MS (ESI, Method B) 328 (M+H)

Example 61

5-(3-Bromo-phenyl)-3-methyl-1H-pyrazolo[4,3-c]isoquinoline a) 3-Bromo-N-(3-methyl-5-phenyl-1H-pyrazol-4-yl)-benzamide (AE1)

The preparation was carried out as in Example 60 (AD) using 385 mg of benzoyl chloride to give the title compound as a pale yellow solid.

HPLC (Method A) R$_T$ 2.68 min

C$_{17}$H$_{14}$BrN$_3$O 355.03 MS (ESI, Method A) 356.06 b) 5-(3-Bromo-phenyl)-3-methyl-1H-pyrazolo[4,3-c]isoquinoline (AE)

The title compound is prepared in an analogous manner as described herein.

Example 62

7-Bromo-3-methyl-5-phenyl-1H-pyrazolo[4,3-c]isoquinoline a) N-[5-(4-Bromo-phenyl)-3-methyl-1H-pyrazol-4-yl]-benzamide (AF1)

The preparation took place in analogy to Example 22A (A1), using 504 mg of 4-amino-5-(4-bromo-phenyl)-3-methyl-pyrazole (Lankau et al, Pharmazie (1999), 54(9), 705–706), except the reaction mixture was stirred for 16 h at which time filtration gave the title compound as a white solid, melting point 273–4° C.

HPLC (Method A) $R_T$ 2.12 min $C_{16}H_{13}BRN_4O$ 356.03, MS (ESI, Method A) 357 (M+H)

b) 7-Bromo-3-methyl-5-phenyl-1H-pyrazolo[4,3-c]isoquinoline (AF)

The preparation took place in analogy to Example 34 (D) using 756 mg of N-[5-(4-bromo-phenyl)-3-methyl-1H-pyrazol-4-yl]-benzamide, except the reaction mixture was refluxed for 2 h and the residue was purified by MPLC (4/1 ethyl acetate/heptane) to give the title compound as a white solid, melting point 299–300° C.

HPLC (Method A) $R_T$ 3.65 min $C_{17}H_{12}BRN_3$ 337.02, MS (ESI, Method A) 338 (M+H)

Example 63

7-Bromo-3-methyl-5-pyrid-3-yl-1H-pyrazolo[4,3-c]isoquinoline a) N-[5-(4-Bromo-phenyl)-3-methyl-1H-pyrazol-4-yl]-nicotinamide (AG1)

The preparation took place in analogy to Example 22A (A1), using 756 mg of 4-amino-5-(4-bromo-phenyl)-3-methyl-pyrazole, except the reaction mixture was stirred for 16 h. The white precipitate in the reaction mixture was filtered, washed with water and dichloromethane, and dried to give the title compound, melting point 262–4° C.

HPLC (Method A) $R_T$ 2.12 min $C_{16}H_{13}BRN_4O$ 356.02 MS (ESI, Method A) 357.04 (M+H)

b) 7-Bromo-3-methyl-5-pyrid-3-yl-1H-pyrazolo[4,3-c]isoquinoline (AJ)

The title compound is prepared in an analogous manner as described herein.

Example 64

5-(2,5-Dimethyl-furan-3-yl)-3-methyl-1H-pyrazolo[4,3-c]isoquinoline a) 2,5-Dimethyl-furan-3-carboxylic acid (3-methyl-5-phenyl-1H-pyrazol-4-yl)-amide (AI1)

The preparation took place in analogy to Example 35 (E1) starting with 424.5 mg of 2,5-dimethyl-3-furoyl chloride. The title compound was obtained as an orange solid.

HPLC (Method A) $R_T$=2.80 min.

$C_{17}H_{17}N_3O_2$ (295.34) MS (ESI, Method A) 296 (M+H).

b) 5-(2,5-Dimethyl-furan-3-yl)-3-methyl-1H-pyrazolo[4,3-c]isoquinoline (AI)

The preparation took place in analogy to Example 34 (D) starting with 562.8 mg of 2,5-dimethyl-furan-3-carboxylic acid (3-methyl-5-phenyl-1H-pyrazol-4-yl)-amide, except the residue was purified by means of MPLC (4 g $SiO_2$, 35% ethyl acetate:dichloromethane) to give the title compound as an orange solid.

HPLC (Method B) $R_T$=3.22 min.

$C_{17}H_{15}N_3O$ (277.33) MS (ESI, Method B) 278 (M+H).

Example 65

3-Methyl-5-thiophen-3-yl-1H-pyrazolo[4,3-c]isoquinoline a) Thiophene-3-carboxylic acid (3-methyl-5-phenyl-1H-pyrazol-4-yl)-amide (AJ1)

The preparation took place in analogy to Example 35 (E1) starting with 403.5 mg of 3-thiophenecarbonyl chloride. The title compound was obtained as a yellow/orange solid.

HPLC (Method A) $R_T$=2.55 min.

$C_{15}H_{13}N_3OS$ (283.35) MS (ESI, Method A) 284 (M+H).

b) 3-Methyl-5-thiophen-3-yl-1H-pyrazolo[4,3-c]isoquinoline (AJ)

The preparation took place in analogy to Example 34 (D) starting with 683.3 mg of thiophene-3-carboxylic acid (3-methyl-5-phenyl-1H-pyrazol-4-yl)-amide, except the residue was purified by recrystallization from dichloromethane. The title compound was obtained as a tan solid.

HPLC (Method B) $R_T$=3.14 min.

$C_{15}H_{11}N_3S$ (265.34) MS (ESI, Method B) 265 (M+H).

Example 66

6-Dimethylamino-5-phenyl-3-methyl-1H-pyrazolo[4,3-c]isoquinoline a) 1-(3-Dimethylamino)-phenylbutan-1,3-dione (AK4)

This compound was prepared by the procedure of Popic et al (Synthesis, 1991, 195), using 8.15 g of (3-dimethylamino)-acetophenone, the reaction taking 20 h to complete. The residue was purified by means of the copper chelate to give the title compound as a green solid.

$C_{12}H_{15}NO_2$ 205 MS (ESI, Method B) 206 (M+H)

b) 1-(3-Dimethylamino)-phenylbutan-1,2,3-trione 2-oxime (AK3)

The preparation was carried out as in Example 22(b), except the reaction mixture was stirred at rt for 4 h. Water was added and the mixture was extracted with ethyl acetate. The organic portions were washed with water and brine, dried over magnesium sulfate, filtered and concentrated to give the title compound as a yellow/green solid.

$C_{12}H_{14}N_2O_3$ 234 MS (ESI, Method B) 235 (M+H)

c) 4-Amino-5-(3-dimethylamino-phenyl)-3-methylpyrazole (AK2)

A solution of 1.25 g of 1-(3-dimethylamino)-phenylbutan-1,2,3-trione 2-oxime in 40 ml of ethanol was treated with 2.8 ml of hydrazine hydrate at 5° C. and stirred at this temperature for 1 h before stirring at rt for 20 h. The reaction mixture was concentrated to leave a tan solid, which was triturated with ether to give the title compound as a tan solid.

$C_{12}H_{16}N_4$ 216 MS (ESI, Method B) 217 (M+H)

d) N-[5-(3-Dimethylamino-phenyl)-3-methyl-1H-pyrazol-4-yl]-benzamide (AK1)

The preparation was carried out as in Example 22A, using 460 mg of benzoyl chloride and 700 mg of 4-amino-5-(3-dimethylamino-phenyl)-3-methylpyrazole, except the reaction mixture was stirred for 16 h and the residue was purified by MPLC (ethyl acetate as eluant) to give the title compound as a tan solid.

HPLC (Method B) $R_T$ 2.55 min
$C_{19}H_{20}N_4O$ 320 MS (ESI, Method B) 321 (M+H)

e) 6-Dimethylamino-5-phenyl-3-methyl-1H-pyrazolo[4,3-c]isoquinoline (AK)

The preparation was carried out as in Example 22A, using 660 mg of N-[5-(3-dimethylamino-phenyl)-3-methyl-1H-pyrazol-4-yl]-benzamide. The residue was purified by MPLC (4/1 ethyl acetate:heptane as eluant) to give the title compound as a yellow solid, which was the less polar component of the residue.

HPLC (Method B) $R_T$ 3.083 min
$C_{19}H_{18}N_4$ 302 MS (ESI, Method B) 303 (M+H)

Example 67

8-Dimethylamino-5-phenyl-3-methyl-1H-pyrazolo[4,3-c]isoquinoline

The title compound was isolated as the more polar component of Example 66 (AK), as a yellow solid.

HPLC (Method B) $R_T$ 3.076 min
$C_{19}H_{18}N_4$ 302 MS (ESI, Method B) 303 (M+H)

Example 68

3-Methyl-5-(2-methylsulfanyl-pyridin-3-yl)-1H-pyrazolo[4,3-c]isoquinoline a) N-(3-methyl-5-phenyl-1H-pyrazol-4-yl)-2-methylsulfanyl-nicotinamide (AL1)

The preparation took place in analogy to Example 35 (E1) starting with 489.2 mg of 2-(methylthio)nicotinoyl chloride. The title compound was obtained as an off-white solid.

HPLC $R_T$=2.54 min.
$C_{17}H_{16}N_4OS$ (324.41) MS (ESI, Method A) 325 (M+H).

b) 5-(2,5-Dimethyl-furan-3-yl)-3-methyl-1H-pyrazolo[4,3-c]isoquinoline (AL)

The preparation took place in analogy to Example 34 (D) starting, with 263.8 mg of N-(3-methyl-5-phenyl-1H-pyrazol-4-yl)-2-methylsulfanyl-nicotinamide, except the residue was purified by means of MPLC (4 g $SiO_2$, 35% ethyl acetate:dichloromethane) to give the title compound as a colorless solid.

HPLC (Method B) $R_T$=3.35 min.
$C_{17}H_{14}N_4S$ (306.39) MS (ESI, Method B) 307 (M+H).

Example 69

5-Methoxymethyl-3-methyl-1H-pyrazolo[4,3-c]isoquinoline a) 2-Methoxy-N-(3-methyl-5-phenyl-1H-pyrazol-4-yl)-acetamide (BA1).

To a RT solution of 416 mg of 3-methyl-5-phenyl-1H-pyrazol-4-ylamine in 4.6 mL pyridine was added 242 μL of methoxyacetyl chloride. After 2 h at RT, the reaction mixture was concentrated under reduced pressure and the residue was dissolved in chloroform and washed with 0.5 N hydrochloric acid and saturated aqueous sodium carbonate and brine. The organic portion was dried with sodium sulfate and concentrated under reduced pressure. The residue contained the title compound as a tan, amorphous solid and was used without further purification.

HPLC $R_T$=1.80 min.
$C_{13}H_{15}N_3O_2$ (245.29) MS (ESI) 246 (M+H).

b) 5-Methoxymethyl-3-methyl-1H-pyrazolo[4,3-c]isoquinoline (BA).

To a suspension of 320 mg of 2-methoxy-N-(3-methyl-5-phenyl-1H-pyrazol-4-yl)-acetamide in 6 mL of phosphorous oxychloride was added 2.70 g of phosphorous pentoxide and the resulting suspension was heated at 120° C. for 5 h. The reaction mixture was cooled to rt and quenched with the addition of ice and water and then neutralized with solid sodium carbonate. The aqueous mixture was extracted with ethyl acetate and the combined organic extracts were washed with brine, dried (magnesium sulfate) and concentrated under reduced pressure. The residue was purified by recrystallisation from ethyl acetate. The title compound was obtained as a reddish, tan solid.

HPLC $R_T$=2.42 min.
$C_{13}H_{13}N_3O$ (227.27) MS (ESI) 228 (M+H).

Example 70

1-Benzyl-5-cyclohexyl-3-methyl-1H-pyrazolo[4,3-c]isoquinoline a) 1-Benzyl-3-methyl-5-phenyl-1H-pyrazol-4-ylamine (BB2).

To a 0° C. solution of 2.32 g of 1-phenyl-butane-1,2,3-trione 2-oxime in 31 mL of EtOH was added a suspension of 2.43 g benzyl hydrazine dihydrochloride in 9 mL EtOH. The reaction mixture was warmed to rt and stirred for 96 h. The reaction mixture was concentrated under reduced pressure and purified by means of MPLC (120 g $SiO_2$, 45% EtOAc:Heptane) to obtain 1-benzyl-3-methyl-4-nitroso-5-phenyl-1H-pyrazole. A suspension of 2.55 g 1-benzyl-3-methyl-4-nitroso-5-phenyl-1H-pyrazole, 34 mL EtOAc and 500 mg 10% Pd/C was reacted under 40 psi $H_2$ atmosphere using a Parr apparatus. After 4 h, the suspension was filtered through Celite (EtOH eluting) and the filtrate was concentrated under reduced pressure and purified by means of MPLC (120 g $SiO_2$, 60% EtOAc:Heptane) to give the title compound as an orange oil.

HPLC $R_T$=2.02 min.
$C_{17}H_{17}N_3$ (263.36) MS (ESI) 264 (M+H).

b) Cyclohexanecarboxylic acid (1-benzyl-3-methyl-5-phenyl-1H-pyrazol-4-yl)-amide (BB1).

To a rt solution of 445 mg of 1-benzyl-3-methyl-5-phenyl-1H-pyrazol-4-ylamine_in 3.6 mL pyridine was added 250 μL of cyclohexanecarbonyl chloride. After 2 h at RT, the reaction mixture was concentrated under reduced pressure and the residue was dissolved in chloroform and washed with 0.5 N hydrochloric acid and saturated aqueous sodium carbonate and brine. The organic portion was dried with sodium sulfate and concentrated under reduced pressure. The residue contained the title compound as a light yellow, amorphous solid and was used without further purification.

HPLC $R_T$=3.18 min.
$C_{24}H_{27}N_3O$ (373.52) MS (ESI) 374 (M+H).

c) 1-Benzyl-5-cyclohexyl-3-methyl-1H-pyrazolo[4,3-c]isoquinoline (BB).

To a suspension of 462 mg of cyclohexanecarboxylic acid (1-benzyl-3-methyl-5-phenyl-1H-pyrazol-4-yl)-amide thiophene-2-carboxylic acid (3-methyl-5-phenyl-1H-pyrazol-4-yl)-amide in 5.6 mL of phosphorous oxychloride was added 2.57 g of phosphorous pentoxide and the resulting suspension was heated at 120° C. for 5 h. The reaction mixture was cooled to rt and quenched with the addition of ice and water and then neutralized with solid sodium carbonate. The aqueous mixture was extracted with ethyl acetate and the combined organic extracts were washed with brine, dried (magnesium sulfate) and concentrated under reduced pressure. The residue was purified by means of MPLC (12 g $SiO_2$, 40% EtOAc:Heptane) to give the title compound as a tan solid.

HPLC $R_T$=4.35 min.

$C_{24}H_{25}N_3$ (355.51) MS (ESI) 356 (M+H).

Example 71

1-Benzyl-5-naphth-2-yl-3-methyl-1H-pyrazolo[4,3-c]isoquinoline a) Naphthalene-2-carboxylic acid (1-benzyl-3-methyl-5-phenyl-1H-pyrazol-4-yl)-amide (BC1).

The preparation took place in analogy to Example 70 (BB1) starting with 275.0 mg of 2-naphthoyl chloride, except the reaction was stirred for 1 h and the product was purified by MPLC (4 g $SiO_2$, 30% EtOAc:Heptane) to give the title compound as a light yellow solid.

HPLC $R_T$=3.32 min.

$C_{28}H_{23}N_3O$ (417.53) MS (ESI) 418 (M+H).

b) 1-Benzyl-5-naphth-2-yl-3-methyl-1H-pyrazolo[4,3-c]isoquinoline (BC)

The title compound is prepared in an analogous manner as described herein.

Example 72

3-Methyl-5-(4-trifluoromethyl-phenyl)-1H-pyrazole[4,3-c]isoquinoline a) N-(3-methyl-5-phenyl-1H-pyrazole-4-yl)-4-trifluoromethyl-benzamide (BD1)

361 mg of 4-trifluoromethylbenzoyl chloride were added dropwise to a solution of 300 mg of 3-methyl-5-phenyl-1H-pyrazol-4-ylamine in 5 ml of pyridine at room temperature. The reaction mixture was stirred for 16 h and then concentrated. The residue was extracted into dichloromethane and washed with 0.5M hydrochloric acid, at which point the title compound precipitated.

HPLC $R_T$ 2.77 min $C_{18}H_{14}F_3N_3O$ 345.32 MS (ESI, method A) 346 (M+H)

b) 3-Methyl-5-(4-trifluoromethyl-phenyl)-1H-pyrazole[4,3-c]isoquinoline (BD)

A solution of 393 mg of N-(3-methyl-5-phenyl-1H-pyrazole-4-yl)-4-trifluoromethyl-benzamide in 15 ml of phosphorus-oxychloride was treated with 2.557 g of phosphorus pentoxide and stirred at 120° C. for 32 hours. The reaction mixture was concentrated and the residue poured carefully onto ice water. The mixture was neutralized with sodium hydrogen carbonate and extracted with ethyl acetate. The organic portion was dried over magnesium sulfate, filtered and concentrated to give a solid., Purification by MPLC (5 g $SiO_2$, ethyl acetate/heptane, gradient of 10/90→100/0) gave the title compound.

HPLC $R_T$ 3.54 min.

$C_{18}H_{12}F_3N_3$ (327.31) MS (ESI, method A) 328 (M+H)

Example 73

3-Methyl-5-(2-trifluoromethyl-phenyl)-1H-pyrazole[4,3-c]isoquinoline a) N-(3-Methyl-5-phenyl-1H-pyrazol-4-yl)-2-trifluoromethyl-benzamide (BE1)

The preparation took place in analogy with Example 72 (BD1), using 317 mg of 2-trifluoromethyl-benzoyl chloride, except the title compound was isolated by filtration directly from the reaction mixture.

HPLC $R_T$ 2.54 min $C_{18}H_{14}F_3N_3O$ (345.33) MS (ESI, method A) 346 (M+1)

b) 3-Methyl-5-(2-trifluoromethyl-phenyl)-1H-pyrazole[4,3-c]isoquinoline (BE)

A solution of 174 mg of N-(3-methyl-5-phenyl-1H-pyrazole-4-yl)-2-trifluoromethyl-benzamide and 67 µl of phosphorus oxychloride in 2 ml of nitrobenzene was heated at 185° C. After 1 h 118 µl of $SnCl_4$ solution (1.0M in heptane) was added and the reaction heated for a further 2 hours. The reaction mixture was concentrated and purified by MPLC (4 g $SiO_2$, ethyl acetate/heptane, gradient of 50/50→100/0, then ethyl acetate/methanol, gradient of 95/5→80/20) to give the title compound.

HPLC $R_T$ 2.92 min $C_{18}H_{12}F_3N_3$ (327.31) MS (ESI, method A) 328 (M+1)

Example 74

3-Methyl-5-(3-trifluoromethyl-phenyl)-1H-pyrazolo[4,3-c]isoquinoline, trifluoroacetic acid salt a) N-(3-Methyl-5-phenyl-1H-pyrazol-4-yl)-3-trifluoromethyl-benzamide (BF1)

The preparation took place in analogy to Example 72 (BD1), starting with 317 mg of 3-(trifluoromethyl)benzoyl chloride and stirring for 24 h before concentrating. Trituration of the residue with a solution of methanol/dichloromethane (5/95) gave the title compound as a white precipitate.

HPLC $R_T$ 2.75 min $C_{18}H_{14}F_3N_3O$ (345.33) MS (ESI, method A) 346(M+H)

b) 3-Methyl-5-(3-trifluoromethyl-phenyl)-1H-pyrazolo[4,3-c]isoquinoline, trifluoroacetic acid salt (BF)

The preparation took place in analogy to Example 73 (BE), using 305 mg of N-(3-methyl-5-phenyl-1H-pyrazol-4-yl)-3-trifluoromethyl-benzamide, except the residue was purified by HPLC (Monochrome 10u C18, 100×21.2 mm column, water (0.1% trifluoroacetic acid)/acetonitrile (0.1% trifluoroacetic acid), gradient=95/5→0/100) to give the title compound.

HPLC $R_T$ 3.31 min $C_{18}H_{12}F_3N_3$ (327.10) MS (ESI, method A) 328 (M+H)

Example 75

5-phenyl-3-trifluoromethyl-1H-pyrazolo[4,3-c]isoquinoline a) 4-Amino-5-phenyl-3-trifluoromethyl-1H-pyrazole (BG2)

A solution of 6.6 g of 4-nitroso-5-phenyl-3-trifluoromethyl-1H-pyrazole (prepared as in Saloutin et al, J. Flourine Chem, vol 84, pp 107–111) in 200 mL ethanol was treated with 2.0 g 10% palladium/carbon catalyst and hydrogenated at RT and 50 psi for 7.5 hours. The reaction mixture was filtered through celite and washed well with ethanol. The filtrate was concentrated to give the title compound as a yellow solid.

$C_{10}H_8F_3N_3$ (227.20), MS (ESI, method B) 228(M+H).

TLC (1/1 ethyl acetate/heptane) $R_f$=0.35.

b) N-(5-Phenyl-3-trifluoromethyl-1H-pyrazol-4-yl)-benzamide (BG1)

A solution of 1.0 g of 4-amino-5-phenyl-3-trifluoromethyl-1H-pyrazole in 30 mL of dichloromethane was treated with 1.1 mL of pyridine followed by 0.57 mL of benzoyl chloride. The reaction mixture was stirred at RT for 5 hours and then concentrated. The residue was partitioned between ethyl acetate and water. The organic portion was washed with brine, dried over magnesium sulfate, filtered and concentrated. The residue was purified by MPLC, eluting with 2/3 ethyl acetate/heptane, to give the title compound as a white solid, melting point 229–230° C.

$C_{17}H_{12}F_3N_3O$ (331.31), MS (ESI, method B) 330 (M–H).

c) 5-Phenyl-3-trifluoromethyl-1H-pyrazolo[4,3-c]isoquinoline (BG).

A mixture of 1.02 g of N-(5-phenyl-3-trifluoromethyl-1H-pyrazol-4-yl)-benzamide in 10 mL of nitrobenzene was treated with 0.41 mL of phosphorous oxychloride and stirred at 185° C. for 6 h. The solvent was distilled off under high vacuum and the residue was partitioned between ethyl acetate and water. The organic portion was washed with saturated sodium bicarbonate, water and brine and dried over magnesium sulphate. Concentration and purification by MPLC, eluting with 1/3 ethyl acetate/heptane, gave the title compound as a white solid, melting point 264–265° C.

HPLC $R_T$ 3.32 min $C_{17}H_{10}F_3N_3$ (313.29), MS (ESI, method B) 314 (M+H).

Example 76

5-(Pyridin-2-yl)-3-trifluoromethyl-1H-pyrazolo[4,3-c]isoquinoline a) N-(Pyridin-2-yl)-(5-phenyl-3-trifluoromethyl-1H-pyrazol-4-yl)amide (BH1)

A solution of 1.0 g of 4-amino-5-phenyl-3-trifluoromethyl-1H-pyrazole in 30 mL of dichloromethane was treated with 1.1 mL of pyridine followed by 0.94 g of picolyl chloride. The reaction mixture was stirred at RT for 24 hours and concentrated. The residue was partitioned between ethyl acetate and water. The organic portion was washed with brine, dried over magnesium sulfate, filtered and concentrated. The residue was purified by MPLC, eluting with 3/7 ethyl acetate/heptane, to give the title compound as a yellow semi-solid.

$C_{16}H_{11}F_3N_4O$ (332.31), MS (ESI, method B) 331 (M–H)

TLC (1/1 ethyl acetate/heptane) $R_f$=0.50.

d) 5-(Pyridin-2-yl)-3-trifluoromethyl-1H-pyrazolo[4,3-c]isoquinoline (BH)

The preparation was carried out as in Example 75 (BG), using 1.02 g of N-(pyridin-2-yl)-(5-phenyl-3-trifluoromethyl-1H-pyrazol-4-yl)-amide, except the reaction mixture was concentrated, then partitioned between ethyl acetate and water. The organic portion was washed with saturated-sodium bicarbonate, water and brine, dried over magnesium sulphate and concentrated. The residue was purified by MPLC, eluting with 1/1 ethyl acetate/heptane, giving the title compound as a beige solid.

HPLC $R_T$ 2.77 min $C_{16}H_9F_3N_4$ (314.29), MS (ESI, method B) 315 (M+H).

Pharmacological Examples

Example 77

The pyrazoloisoquinoline derivatives according to the invention were tested for inhibitory activity against NIK in various in vitro assay systems. In this connection, human peripheral blood lymphocytes were preincubated for 1 h with different concentrations of the compounds and then stimulated for 24 h with LPS or IL1β. After that, a commercially obtainable ELISA test kit was used to measure the release of TNFα in the culture supernatant, and the IC50 for the given compound was determined. The cytotoxicity was measured by way of LDH release using a commercially obtainable test kit and the LD50 for the given compound was determined.

In another assay, heparinized whole human blood was preincubated for 1 h with different concentrations of the compounds and then stimulated with LPS for 24 h. Commercially available test kits were used to measure the release of IL1β, TNFα and IL6 in the supernatant after 24 h, and the IC50 for the given compound was determined.

The results are shown in the following tables 1, 2 and 3.

TABLE 1

Inhibition of TNFα release in LPS-stimulated human peripheral blood lymphocytes:

| Example No. | TNFα release IC50 (µM) | IL6 release IC50 (µM) | Cytotoxicity LD50 (µM) |
|---|---|---|---|
| 1 | 1.9 | 80 | >100 |
| 2 | 9 | >100 | >100 |
| 3 | 7.5 | 80 | >100 |

The sign ">" denotes greater than

TABLE 2

Inhibition of TNFα release in IL1β-stimulated human peripheral blood lymphocytes:

| Example No. | TNFα release IC50 (µM) | IL6 release IC50 (µM) | Cytotoxicity LD50 (µM) |
|---|---|---|---|
| 1 | 5 | 80 | >100 |
| 2 | 35 | >100 | >100 |
| 3 | 8 | >100 | >100 |

TABLE 3

Inhibition of the release of IL1β, TNFα and IL6 in LPS-stimulated heparinized whole human blood:

| Example No. | IL1β release IC50 (μM) | TNFα release IC50 (μM) | IL6 release IC50 (μM) |
| --- | --- | --- | --- |
| 1 | 33 | 12.5 | >100 |
| 2 | 1.3 | 1.2 | 7 |
| 3 | 29 | 5 | >100 |

Example 78

EAE Model

This example illustrates the efficacy of the compounds of this invention in the treatment of multiple sclerosis. As described herein, experimental autoimmune encephalomyelitis (EAE) model is used to show such an efficacy. The following procedures are employed in this model.

Animals:

SJL/J female mice, 8 wks. old, are obtained from Jackson Laboratories.

Antigens:

Myelin Proteolipid Protein (PLP 139–151) (HSLGK-WLGHPDKF) (Cat #H-2478) is obtained from BACHEM, Bioscience, Inc., 3700 Horizon Dr., King of Prussia, Pa. 19406, 1-610-239-0300 (phone), 1-610-239-0800 (fax).

Complete Freund's Adjuvant H37 Ra [1 mg/ml *Mycobacterium Tuberculosis* H37 Ra] is obtained from Difco 1-800-521-0851 (Cat #3114-60-5, 6×10 ml).

*Mycobacterium Tuberculosis* is also obtained from Difco, 1-800-521-0851 (Cat #3114-33-8, 6×100 mg).

*Pertussis* Toxin

*Bordetella Pertussis*, (Lyophilized powder containing PBS and lactose) is obtainde from List Biological Laboratories, 1-408-866-6363 (Product #180, 50 ug @ $140.00 ea.).

Induction of EAE in Mice

PLP139–151 peptide is dissolved in $H_2O$:PBS (1:1) solution to a concentration of 7.5 mg/10 ml (for 75 ug PLP per group) and emulsified with an equal volume of CFA supplemented with 40 mg/10 ml heated-killed *mycobacterium tuberculosis* H37Ra. Mice are injected s.c. with 0.2 ml of peptide emulsion in the abdominal flank (0.1 ml on each side). On the same day and 72 hours later, mice are injected i.v. with 100□l of 35 ng and 50 ng of *Bordetella Pertussis* toxin in saline respectively.

Clinical Assessment

STAGE 0: Normal
STAGE 0.5: Partial limp tail
STAGE 1: Complete Limp Tail
STAGE 2: Impaired righting reflex
STAGE 2.5: Righting reflex is delayed (Not weak enough to be stage 3).
STAGE 3: Partial hind limb paralysis
STAGE 3.5: One leg is completely paralyzed, and one leg is partially paralyzed,
STAGE 4: Complete hind limb paralysis
STAGE 4.5: Legs are completely paralyzed and Moribund
STAGE 5: Death due to EAE Clinical Courses of EAE Acute phase: First clinical episode (Day 10–18)

Remission: Phase of clinical improvement following a clinical episode; characterized by a reduction (>=one grade) in clinical score for at least two days after the peak score of acute phase or a disease relapse.

Relapse: Increase of at least one grade in clinical score for at least two days after remission has been attained.

The animals treated with the compounds of this invention generally would be expected to show improvements in clinical scores.

Example 79

This Example illustrates the efficacy of the compounds of this invention by way of inhibiting NIK-mediated release of IL-1β, from human macrophages activated by the Alzheimer's beta amyloid peptide 1–42.

Cell isolation: Monocytes are isolated from peripheral blood mononuclear cells (PBMCs) as follows. Whole blood is layered directly onto Histopak 1077-1 columns (Sigma Biochemicals) and centrifuged at 800×g for 15 minutes. The PBMC band of cells is removed to a fresh 50 ml culture tube and diluted 1:1 with wash buffer (Phosphate buffered saline, pH 7.4 containing 2 mM EDTA and 5 mg/ml BSA) followed by centrifugation at 800×g for 5 minutes. Cells are then washed by sequential resuspension of the cell pellet in wash buffer and centrifugation at 600×g for 5 minutes. The wash process is repeated until the supernatent is clear of contaminating platelets (5 to 6 washes). Monocytes are then purified from the PBMCs by negative selection using a monocyte isolation kit (Miltenyi Biotec, Inc) that contains antibodies to non-monocytic cells, running the cells over a magnetic column to remove antibody-bound cells, and collecting the flow through volume of monocytes. Monocytes are washed once with wash buffer and seeded at 10E5 cells per well in 100 μl serum-free RPMI 1640 in 96-well plates and incubated for 1 hour at 37° C. in a 5% $CO_2$/95% humidified tissue culture incubator. After 1 hour, the medium is replaced with 100 μl complete culture medium (RPMI 1640, 10% human serum-type AB (heat inactivated), 25 mM HEPES, 2 mM glutamine, 50 U/ml each of penicillin and streptomycin) and incubated overnight (16 hours).

Dosing regimen: The next day, the culture medium is replaced with 100 μl fresh complete culture medium in the absence or presence of human beta amyloid 1–42 peptide (5 μM) and incubated at 37° C. in a 5% $CO_2$/95% humidified tissue culture incubator for 5 hours. Medium is then removed and discarded. Each well is washed once with Hanks buffered saline (HBSS) containing 1 mM $CaCl_2$ followed by the addition of 80 μl of HBSS/$CaCl_2$. Samples are then given either 10 μl of HBSS/$CaCl_2$ or 10 μl of the NIK inhibiting compound of the present invention (10× stock in HBSS/$CaCl_2$ for a final concentration of 23 nM and 206 nM) and incubated 15 minutes in the tissue culture incubator followed by the addition of either 10 μl of HBSS/$CaCl_2$ or 10 μl of benzoylbenzoyl ATP (BZATP; 3 mM stock in HBSS/$CaCl_2$ for a 300 μM final concentration) and incubated for a further 30 minutes in the tissue culture incubator. Medium is then removed to new 96-well plates for storage at −70° C. until the IL-1β content is quantitated by ELISA (from R&D Systems). The cells are washed once with HBSS/$CaCl_2$ followed by lysing the cells with 100 μl ice cold lysis buffer (100 mM Tris, pH 7.6, 1% triton X-100, and 1 tablet per 30 ml Complete TM protease inhibitor from Roche Biochemicals, Inc). Cell lysates are stored at −70° C. until the IL-1β is quantitated by ELISA.

The compounds of this invention generally would be expected to show decrease in the BzATP-induced IL-1β secretion.

What is claimed is:

1. A compound selected from the group consisting of:
5-pyridin-2-yl-3-trifluoromethyl-1H-pyrazolo[4,3-c]iso-quionoline,
3-methyl-5-(2-trifluoromethyl-phenyl-1H-pyrazolo[4,3-c]isoquinoline,
3-methyl-5-(3-trifluoromethyl-phenyl)-1H-pyrazolo[4,3-c]isoquinoline,
3-methyl-5-(4-trifluoromethyl-phenyl)-1H-pyrazolo[4,3-c]isoquinoline,
1,3-dimethyl-5-(3-trifluoromethylphenyl)-1H-pyrazolo[4,3-c]-isoquinoline,
5-phenyl-3-trifluoromethyl-1H-pyrazolo[4,3-c]isoquinoline,
1,3-dimethyl-5-(3-trifluoromethylphenyl-1H-pyrazolo[4,3-c]-isoquinoline,
1,3-dimethyl-5-(2,6-difluorophenyl)-1H-pyrazolo[4,3-c]-isoquinoline,
1-benzyl-5-cyclohexyl-3-methyl-1H-pyrazolo[4,3-c]-isoquinoline,
1-benzyl-5-naphthyl-3-methyl-1H-pyrazolo[4,3-c]-isoquinoline,
7methoxycarbonyl-3-methyl-5-phenyl-1H-pyrazolo[4,3-c]-isoquinoline,
7-methoxycarbonyl-3-methyl-5-pyridin-2-yl-1H -pyrazolo[4,3-c]-isoquinoline,
7-dimethylamino-3-methyl-5-phenyl-1H-pyrazolo[4,3-c] isoquinoline,
7-dimethylamino-3-methyl-5pyridin-2-yl-1H-pyrazolo]4,3-c]-isoquinoline,
6-dimethylamino-3-methyl-5-phenyl-1H-pyrazolo[4,3-c]-isoquinoline,
6-dimethylamino-3-methyl-5-pyridin-2-yl-1H-pyrazolo [4,3-c]-isoquinoline,
8-dimethylamino-3-methyl-5-phenyl-1H-pyrazolo[4,3-c] isoquinoline,
8-dimethylamino-3-methyl-5-pyridin-2-yl-1H-pyrazolo [4,3-c]-isoquinoline,
1,3-dimethyl-5-(3-methyl-thiophen-2-yl)-1H-pyrazolo[4,3-c]-isoquinoline,
3-methyl-5-phenyl-9-trifluoromethyl-1H-pyrazolo[4,3-c] isoquinoline,
3-methyl-5-pyridin-2-yl-9-trifluoromethyl-1H-pyrazolo [4,3-c]-isoquinoline, and
3-methyl-5-(2,3,4,5,6-pentafluoro-phenyl)-1H-pyrazolo [4,3-c]-isoquinoline.

2. A pharmaceutical composition comprising a therapeutically effective content of at least one compound as claimed in claim 1 together with a pharmaceutically suitable carrier.

3. A method of treating a disease condition selected from the group consisting of osteoarthritis, rheumatoid arthritis, asthma, comprising administering to a patient suffering from said disease condition a therapeutically effective amount of a compound according to claim 1.

4. The method as claimed in claim 3, wherein the disease condition is osteoarthritis.

5. The method as claimed in claim 3, wherein the disease condition is rheumatoid arthritis.

* * * * *